(12) United States Patent
Pollock et al.

(10) Patent No.: US 12,029,395 B2
(45) Date of Patent: Jul. 9, 2024

(54) INTEGRATED CONTAINER AND TUBE SET FOR FLUID DELIVERY WITH AN ENDOSCOPE

(71) Applicant: BOSTON SCIENTIFIC SCIMED, INC., Maple Grove, MN (US)

(72) Inventors: Ryan Pollock, Sterling, MA (US); Colby Harris, Norfolk, MA (US); Ryan Wales, Northborough, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 18/100,269

(22) Filed: Jan. 23, 2023

(65) Prior Publication Data

US 2023/0157531 A1 May 25, 2023

Related U.S. Application Data

(63) Continuation of application No. 17/558,239, filed on Dec. 21, 2021, now Pat. No. 11,576,566.
(Continued)

(51) Int. Cl.
*A61B 1/12* (2006.01)
*A61B 1/00* (2006.01)
(Continued)

(52) U.S. Cl.
CPC .......... *A61B 1/126* (2013.01); *A61B 1/00119* (2013.01); *A61B 1/00137* (2013.01);
(Continued)

(58) Field of Classification Search
None
See application file for complete search history.

(56) References Cited

U.S. PATENT DOCUMENTS

| 6,286,179 B1 * | 9/2001 | Byrne ................ A61B 1/00128 |
| | | 134/169 C |
| 9,750,398 B2 * | 9/2017 | Adams ............... A61B 1/00119 |

(Continued)

FOREIGN PATENT DOCUMENTS

EP 2476365 A1 7/2012

OTHER PUBLICATIONS

International Search Report and Written Opinion dated Mar. 24, 2022 for International Application No. PCT/US2021/064688.

*Primary Examiner* — Cristi J Tate-Sims
(74) *Attorney, Agent, or Firm* — Seager, Tufte & Wickhem, LLP

(57) ABSTRACT

This disclosure relates generally to a container and tube set and methods for fluid delivery, and particularly an integrated container and tube set suitable for use with an endoscope to supply liquids and/or gases to the endoscope. The integrated container and tubes may include a container (e.g., water reservoir) containing a fluid and a gas, and a plurality of tubes integrally formed with the container. The integrated container may include an irrigation supply tube having a first lumen in fluid communication with the fluid, a lens wash supply tube having a second lumen in fluid communication with the fluid, a gas supply tube having a third lumen in operative communication with the gas, and an optional alternative gas supply tube having a fourth lumen in fluid communication with the gas. The lens wash supply tube and the gas supply tube may be formed as a single, multi-lumen tube.

20 Claims, 14 Drawing Sheets

Related U.S. Application Data

(60) Provisional application No. 63/129,204, filed on Dec. 22, 2020, provisional application No. 63/129,199, filed on Dec. 22, 2020.

(51) Int. Cl.
    *A61B 1/015* (2006.01)
    *B08B 3/04* (2006.01)
    *B08B 5/02* (2006.01)

(52) U.S. Cl.
    CPC .............. *A61B 1/015* (2013.01); *B08B 3/04* (2013.01); *B08B 5/02* (2013.01)

(56) References Cited

U.S. PATENT DOCUMENTS

| | | | |
|---|---|---|---|
| 2006/0229498 A1* | 10/2006 | Kohno | A61B 1/00068 600/158 |
| 2016/0073867 A1 | 3/2016 | Ramsey | |
| 2018/0168439 A1* | 6/2018 | Hibbs | A61B 1/126 |
| 2019/0090725 A1 | 3/2019 | Roberts | |
| 2022/0192479 A1 | 6/2022 | Harris et al. | |

\* cited by examiner

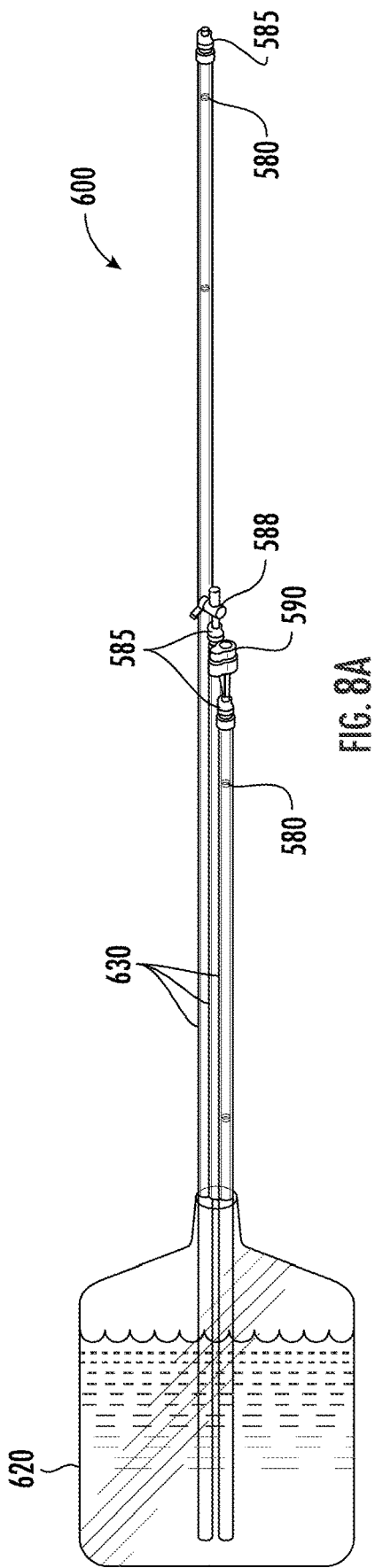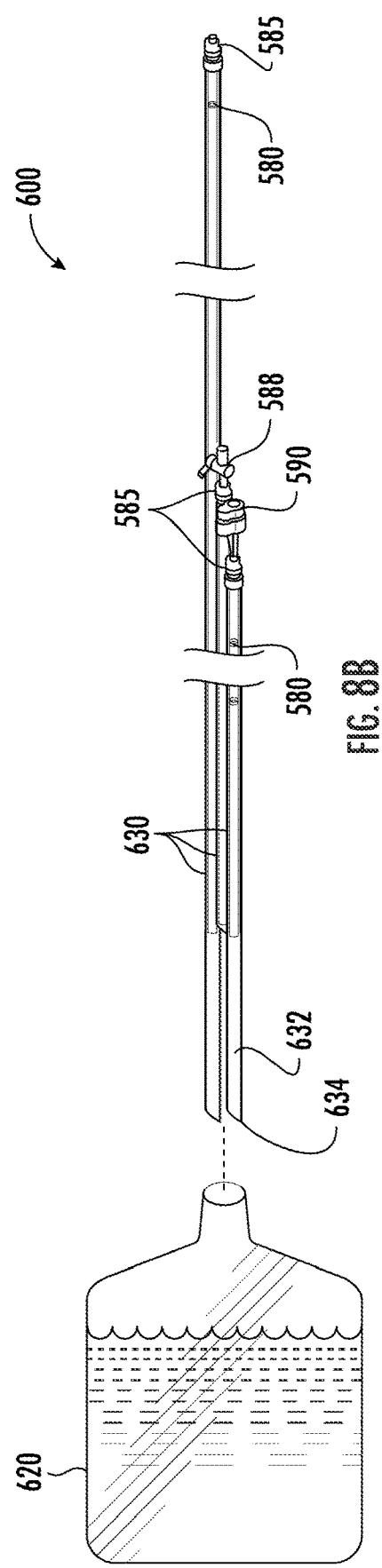

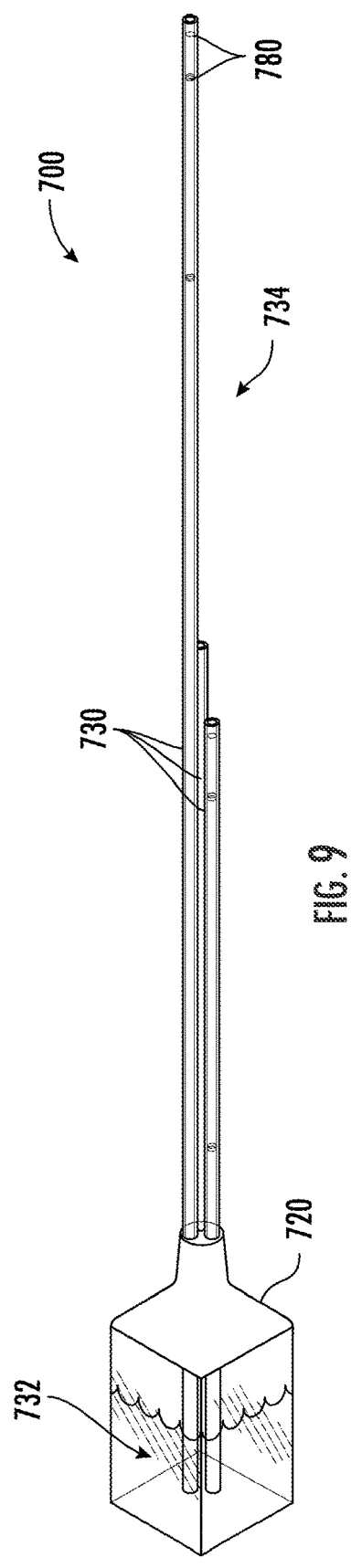
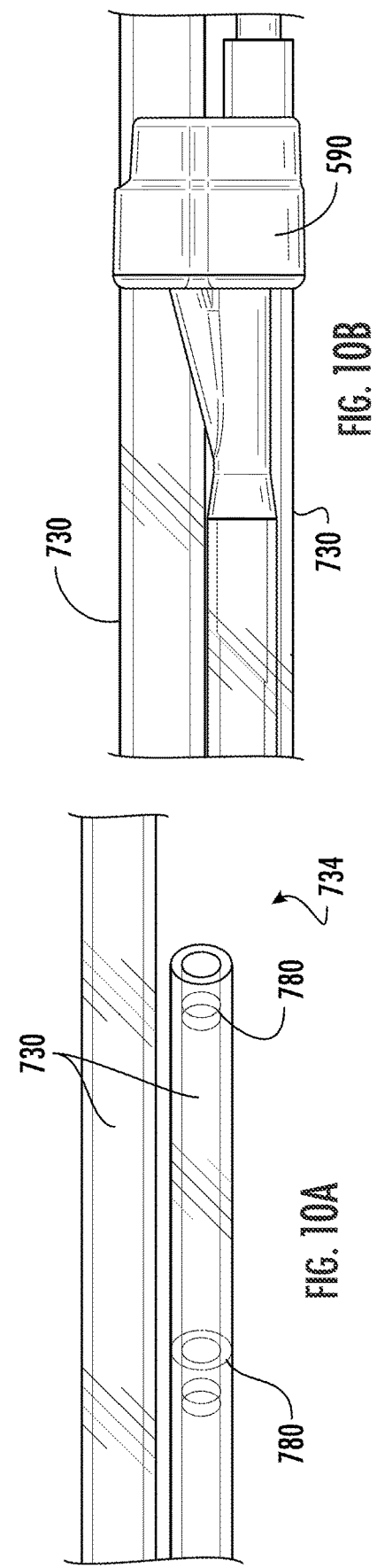

INTEGRATED CONTAINER AND TUBE SET FOR FLUID DELIVERY WITH AN ENDOSCOPE

RELATED APPLICATIONS

This application is a continuation of and claims the benefit of the earlier filing date of U.S. patent application Ser. No. 17/558,239, filed on Dec. 21, 2021, which claims the benefit of priority under 35 U.S.C. § 119 to U.S. Provisional Patent Application No. 63/129,204, titled "Integrated Container and Tube Set for Fluid Delivery with an Endoscope", filed on Dec. 22, 2020, and claims the benefit of priority under 35 U.S.C. § 119 to U.S. Provisional Patent Application No. 63/129,199, titled "Tubing Assemblies and Methods for Fluid Delivery", filed on Dec. 22, 2020, each of which is incorporated herein by reference in its entirety.

FIELD

This disclosure relates generally to medical fluid containers and tubing assemblies and methods for fluid delivery, and particularly to an integrated bottle (e.g., container, reservoir, or the like) and tube assembly to supply fluid and/or gas to an endoscope.

BACKGROUND

Conventionally, endoscope devices have been widely used for performing diagnostic and/or therapeutic treatments. Such endoscope devices sometimes include a fluid capability, or the like, configured to feed fluid to the end of the endoscope for insufflating the inside of the patient at the target site. Lens wash provides a liquid such as sterilized water at relatively high pressure to spray across and clear the camera lens of debris. The water source for lens wash and irrigation typically has included one or more fluid reservoirs with tubing and cap assemblies that creates the plumbing circuit in connection with the endoscope channels and valving to accomplish the gas and water functions described. Such tubing and cap assemblies are available in various configurations, which typically involve a water bottle, a cap fitted for the specific bottle, and an array of tubing that is extendable through openings in the cap. The tubing typically is arranged to accommodate a specific configuration of endoscope fittings and valving.

It is with these considerations in mind that the improvements of the present disclosure may be useful.

SUMMARY

This summary of the disclosure is given to aid understanding, and one of skill in the art will understand that each of the various aspects and features of the disclosure may advantageously be used separately in some instances, or in combination with other aspects and features of the disclosure in other instances. No limitation as to the scope of the claimed subject matter is intended by either the inclusion or non-inclusion of elements, components, or the like in this summary. Accordingly, while the disclosure is presented in terms of aspects or embodiments, it should be appreciated that individual aspects can be claimed separately or in combination with aspects and features of that embodiment or any other embodiment.

According to an aspect, an integrated container and tube set arranged and configured to couple to an endoscope for use in an endoscopic procedure is disclosed. In one embodiment, the integrated container and tube set comprises a container configured to contain a fluid, the container having a bottom portion and a top portion, and a plurality of tubes integrally formed with the container. The plurality of tubes include an irrigation supply tube, a lens wash supply tube, and a gas supply tube. The irrigation supply tube includes a wall that is continuous with the container, the irrigation supply tube including a first end, a second end, and a first lumen extending therethrough, wherein the first end of the irrigation supply tube is in fluid communication with the bottom portion of the container and the second end of the irrigation supply tube is positioned external to the container. The lens wash supply tube includes a wall that is continuous with the container, the lens wash supply tube including a first end, a second end, a second lumen extending therethrough, wherein the first end of the lens wash supply tube is in fluid communication with the bottom portion of the container and the second end of the lens wash supply tube is positioned external to the container. The gas supply tube includes a wall that is continuous with the container, the gas supply tube including a first end, a second end, a third lumen extending therethrough, wherein the first end of the gas supply tube is in operative communication with the top portion of the container and the second end of the gas supply tube is positioned external to the container.

In various of the described and other embodiments within the scope of the present disclosure, the lens wash supply tube and the gas supply tube are arranged and configured as a multi-lumen tube.

In various of the described and other embodiments within the scope of the present disclosure, the second lumen is coaxial with the third lumen, with the second lumen positioned within the third lumen.

In various of the described and other embodiments within the scope of the present disclosure, the multi-lumen tube further comprises an internal wall extending along a length thereof between the second lumen and the third lumen so that the third lumen extends adjacent to the second lumen.

In various of the described and other embodiments within the scope of the present disclosure, each of the second ends of the irrigation supply tube, the lens wash supply tube, and the gas supply tube are sealed.

In various of the described and other embodiments within the scope of the present disclosure, each of the second ends of the irrigation supply tube, the lens wash supply tube, and the gas supply tube are arranged and configured with a one-way valve.

In various of the described and other embodiments within the scope of the present disclosure, at least one of the irrigation supply tube, the lens wash supply tube, and the gas supply tube, includes an adjustable connector coupled thereto, the adjustable connector moveable between a closed position and an opened position.

In various of the described and other embodiments within the scope of the present disclosure, the integrated container and tube set further comprises an endoscope adapter operatively coupled to the lens wash supply tube and the gas supply tube, the endoscope adapter comprising a fluid lumen in fluid communication with the second lumen and a gas lumen in communication with the third lumen, the endoscope adapter configured to interface with an endoscope.

In various of the described and other embodiments within the scope of the present disclosure, the integrated container and tube set further comprises an alternative gas supply tube having a wall that is continuous with the container, the alternative gas supply tube including a first end, a second end, and a fourth lumen extending therethrough, wherein the first end of the alternative gas supply tube is in operative communication with the top portion of the container and the second end of the alternative gas supply tube is positioned external to the container.

In various of the described and other embodiments within the scope of the present disclosure, a stop cock valve is coupled to the second end of the alternative gas supply tube.

In various of the described and other embodiments within the scope of the present disclosure, a pump is in fluid communication with the irrigation supply tube.

In various of the described and other embodiments within the scope of the present disclosure, the irrigation supply tube is configured to fluidly couple the first lumen with an irrigation channel of an endoscope.

In various of the described and other embodiments within the scope of the present disclosure, the container further comprises a supply port formed therein to couple with a fluid supply.

In various of the described and other embodiments within the scope of the present disclosure, the container is overmolded to each of the plurality of tubes.

In various of the described and other embodiments within the scope of the present disclosure, the container further comprises a fluid therein, wherein the fluid is a sterile fluid, the container sealing the sterile fluid from the atmosphere.

According to another aspect, an integrated container and tube set arranged and configured to couple to an endoscope for use during an endoscopic procedure is disclosed. The integrated container and tube set comprises a container configured to contain a fluid, an irrigation supply tube, a lens wash supply tube, and a gas supply tube. The container includes a bottom portion and a top portion. The irrigation supply tube includes a first end, a second end, and a first lumen extending therethrough, wherein the first end of the irrigation supply tube is reversibly coupled to the container, the first end of the irrigation supply tube being arranged and configured to be in fluid communication with the bottom portion of the container, and the second end of the irrigation supply tube is positioned external to the container. The lens wash supply tube includes a first end, a second end, and a second lumen extending therethrough, wherein the first end of the lens wash supply tube is reversibly coupled to the container, the first end of the lens wash supply tube being arranged and configured to be in fluid communication with the bottom portion of the container and the second end of the lens wash supply tube is positioned external to the container. The gas supply tube includes a first end, a second end, and a third lumen extending therethrough, wherein the first end of the gas supply tube is reversibly coupled to the container, the first end of the gas supply tube being arranged and configured to be in operative communication with the top portion of the container and the second end of the gas supply tube is positioned external to the container.

In various of the described and other embodiments within the scope of the present disclosure, the integrated container and tube set further comprises an alternative gas supply tube having a first end, a second end, and a fourth lumen extending therethrough, wherein the first end of the alternative gas supply tube is reversibly coupled to the container, the first end of the alternative gas supply tube being arranged and configured to be in operative communication with the top portion of the container and the second end of the alternative gas supply tube is positioned external to the container.

In various of the described and other embodiments within the scope of the present disclosure, the integrated container and tube set further comprises a penetrating member disposed on the first end of each of the irrigation supply tube, the lens wash supply tube, and the gas supply tube.

In various of the described and other embodiments within the scope of the present disclosure, the irrigation supply tube, the lens wash supply tube, and the gas supply tube are arranged and configured as a multi-lumen tube including the first lumen, the second lumen, and the third lumen.

According to another aspect, an integrated container and tube set arranged and configured to couple to an endoscope for use during an endoscopic procedure is disclosed. The integrated container and tube set comprises a container configured to contain a fluid, an irrigation supply tube, a lens wash supply tube, and a gas supply tube. The container includes a bottom portion and a top portion. The irrigation supply tube includes a wall that is continuous with the container, the irrigation supply tube including a first end, a second end, and a first lumen extending through the first end and along a length of the irrigation supply tube toward the second end of the irrigation supply tube, wherein the first end of the irrigation supply tube is in fluid communication with the bottom portion of the container and the second end of the irrigation supply tube is closed to the first lumen. The lens wash supply tube includes a wall that is continuous with the container, the lens wash supply tube including a first end, a second end, a second lumen extending through the first end of the lens wash supply tube and along a length of the lens wash supply tube toward the second end of the lens wash supply tube, wherein the first end of the lens wash supply tube is in fluid communication with the bottom portion of the container and the second end of the lens wash supply tube is closed to the second lumen. The gas supply tube includes a wall that is continuous with the container, the gas supply tube including a first end, a second end, a third lumen extending through the first end of the gas supply tube and along a length of the gas supply tube toward the second end of the gas supply tube, wherein the first end of the gas supply tube is in operative communication with the top portion of the container and the second end of the gas supply tube is closed to the third lumen.

In various of the described and other embodiments within the scope of the present disclosure, the integrated container and tube set further comprises an alternative gas supply tube having a wall that is continuous with the container, the alternative gas supply tube including a first end, a second end, and a fourth lumen extending through the first end of the alternative gas supply tube and along a length of the alternative gas supply tube toward the second end of the alternative gas supply tube, wherein the first end of the alternative gas supply tube is in operative communication with the top portion of the container and the second end of the alternative gas supply tube is closed to the fourth lumen.

In various of the described and other embodiments within the scope of the present disclosure, each second end of each of the irrigation supply tube, the lens wash supply tube, and the gas supply tube are configured to be penetrated by an adapter member.

According to another aspect, an integrated container and tube set arranged and configured to couple to an endoscope for use during an endoscopic procedure is disclosed. The integrated container and tube set comprise a container configured to contain a fluid, a coaxial tube, and an irrigation supply tube. The container includes an upper half and a lower half. The upper half includes a fill port. The coaxial tube is coupled to the upper half of the container and includes an inner tube and an outer tube. The inner tube includes a lens wash supply tube and terminates in the lower half of the container. The outer tube includes a gas supply tube and terminates in the upper half of the container. The irrigation supply tube is coupled to the lower half of the container and terminates in the lower half of the container.

In various of the described and other embodiments within the scope of the present disclosure, the outer tube is integrally formed with the container.

In various of the described and other embodiments within the scope of the present disclosure, the irrigation supply tube is integrally formed with the container.

In various of the described and other embodiments within the scope of the present disclosure, the integrated container and tube set further comprise an alternative gas supply tube coupled to the upper half of the container. In many embodiments, the alternative gas supply tube terminates in the upper half of the container. In some embodiments, the alternative gas supply tube is integrally formed with the container.

In various of the described and other embodiments within the scope of the present disclosure, the container includes an interface configured to couple the container to a mount or holder. In some embodiments, the interface includes a hook or loop in the upper half of the container.

In various of the described and other embodiments within the scope of the present disclosure, the integrated container and tube set further comprise a gas/lens wash connection attached to an end of the coaxial tube and configured to interface with an endoscope. In some embodiments, the gas/lens wash connection includes a coaxial split connector comprising first and second openings. The first opening may be in fluid communication with the inner tube and the second opening may be in fluid communication with the outer tube.

In various of the described and other embodiments within the scope of the present disclosure, the gas supply tube may include a check valve configured to only allow flow from the gas supply tube into the container. In many embodiments, the coaxial tube may be coupled to the upper half of the container via a coaxial split connector. In many such embodiments, a gas supply port of the coaxial split connector may include a check valve coupled thereto.

In some embodiments, a check valve may be disposed between the gas supply tubing and an interior of the container. In some such embodiments, the check valve is configured only allow flow from the gas supply tubing into the container. In one embodiment, the check valve may include an umbrella style check valve that extends between the inner and out tubes of the coaxial tube to create a one-way seal between the lens wash tubing and the gas supply tube.

In various of the described and other embodiments within the scope of the present disclosure, the container may include a first chamber and a second chamber connected by a side channel. In some such embodiments, the side channel may include a check valve that only allows flow from the second chamber to the first chamber. In various such embodiments, the coaxial tube is coupled to the first chamber. In many embodiments, the side channel may be integrally formed with the container. In some embodiments, the container may be collapsible.

These and other features and advantages of the present disclosure will be readily apparent from the following detailed description, the scope of the claimed invention being set out in the appended claims.

BRIEF DESCRIPTION OF THE DRAWINGS

The accompanying drawings, which are incorporated in and constitute a part of this specification, illustrate various exemplary embodiments and together with the description serve to explain the principles of the present disclosure.

FIG. 8A depicts an alternate embodiment of an integrated container and tube set suitable for use with an endoscope system, wherein the container is a non-rigid container, according to an embodiment of the present disclosure;

FIG. 8B depicts an exploded view of the integrated container and tube set of FIG. 8A, wherein the tubes include a sharpened end portion for piercing the non-rigid container, according to an embodiment of the present disclosure;

FIG. 9 depicts an alternate embodiment of an integrated container and tube set suitable for use with an endoscope system, wherein the tubes include a seal formed in a second end thereof, according to an embodiment of the present disclosure;

FIG. 10A depicts a detailed view of the second end of the tubes of the integrated container and tube set of FIG. 9;

FIG. 10B illustrates a detailed view of the second end of the tubes of the integrated container and tube set of FIG. 9, wherein the second end of one of the tubes includes a coaxial split connector as an adaptor and the second end of one of the tubes includes a stop-cock adaptor, according to an embodiment of the present disclosure;

DETAILED DESCRIPTION

Figure 1:
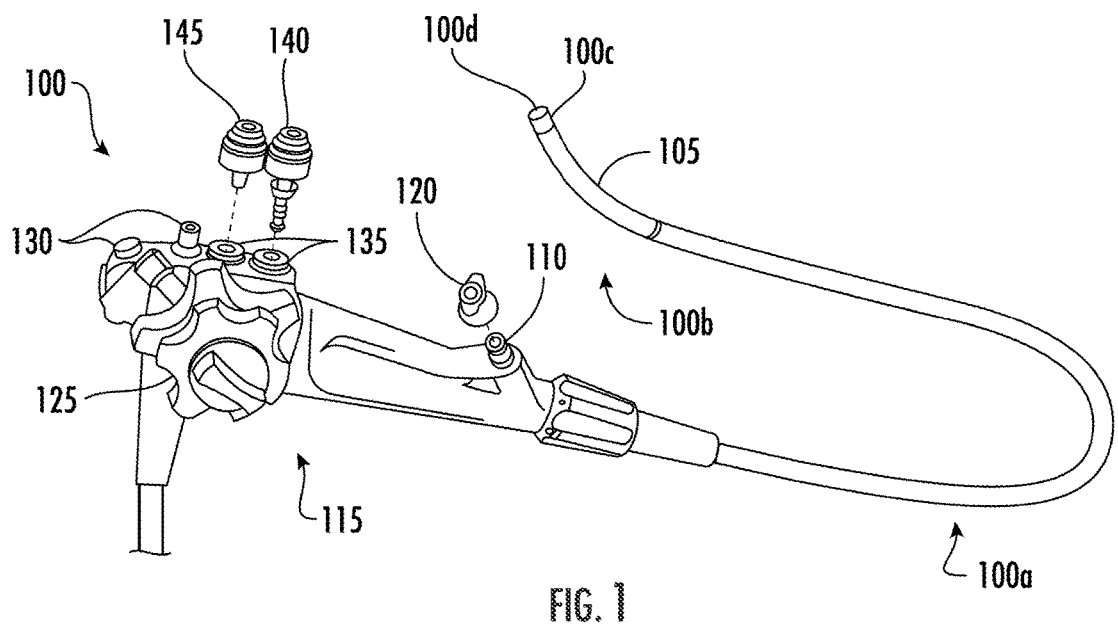
FIG. 1 depicts components of an endoscope.

This disclosure is now described with reference to an exemplary medical system that may be used in endoscopic medical procedures. However, it should be noted that reference to this particular procedure is provided only for convenience and not intended to limit the disclosure. A person of ordinary skill in the art would recognize that the concepts underlying the disclosed devices and related methods of use may be utilized in any suitable procedure, medical or otherwise. This disclosure may be understood with reference to the following description and the appended drawings, wherein like elements are referred to with the same reference numerals.

Wherever possible, the same or similar reference numbers will be used through the drawings to refer to the same or like parts. The term "distal" refers to a portion farthest away from a user when introducing a device into a patient. By contrast, the term "proximal" refers to a portion closest to the user when placing the device into the patient. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal." Further, as used herein, the terms "about," "approximately" and "substantially" indicate a range of values within +/−10% of a stated or implied value. Additionally, terms that indicate the geometric shape of a component/surface refer to exact and approximate shapes.

Although embodiments of the present disclosure are described with specific reference to a bottle (e.g., container, reservoir, or the like) and tube assembly or set, it should be appreciated that such embodiments may be used to supply fluid and/or gas to an endoscope, for a variety of different purposes, including, for example to facilitate insufflation of a patient, lens washing, and/or to irrigate a working channel to aid in flushing/suctioning debris during an endoscopic procedure.

Although the present disclosure includes description of a bottle and tube set suitable for use with an endoscope system to supply fluid and/or gas to an endoscope, the devices, systems, and methods herein could be implemented in other medical systems requiring fluid and/or gas delivery, and for various other purposes.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

Figure 2:
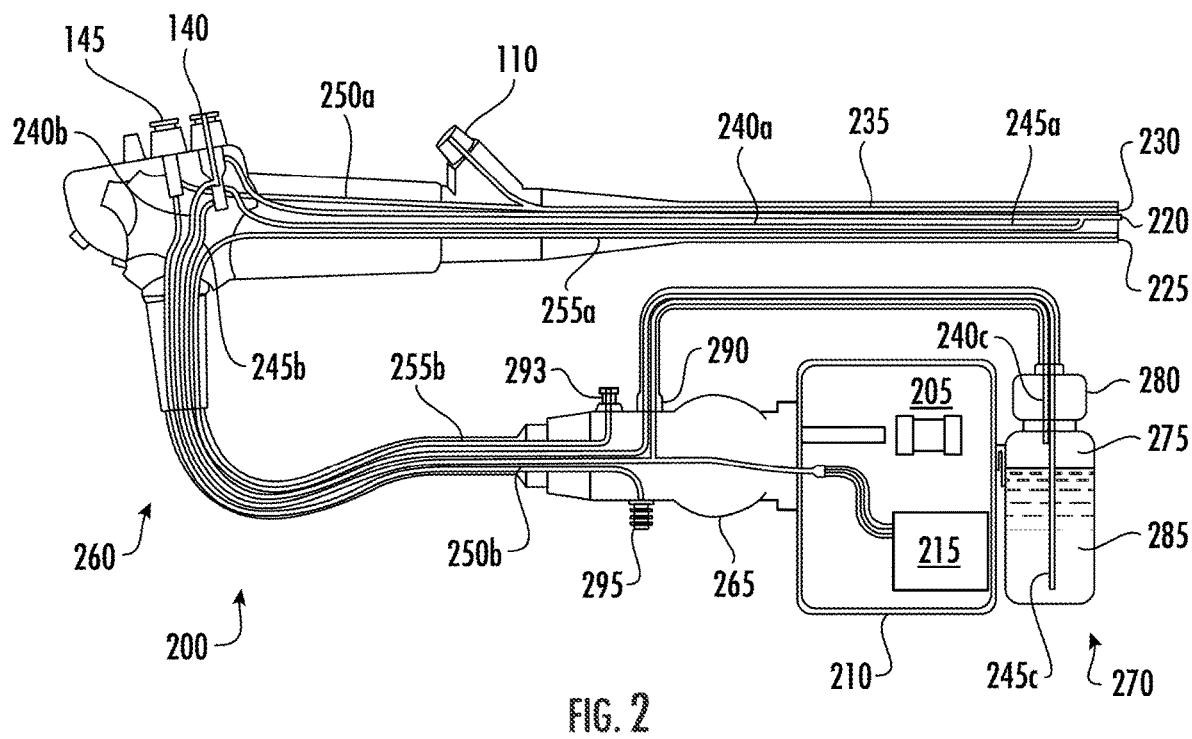
FIG. 2 depicts components of an endoscope system with endoscope, light source, light source connector, water reservoir, and tubing assembly for air and lens wash fluid delivery.

With reference to FIGS. 1-2, an exemplary endoscope 100 and system 200 is depicted that may comprise an elongated shaft 100a that is inserted into a patient. A light source 205 feeds illumination light to a distal portion 100b of the endoscope 100, which may house an imager (e.g., CCD or CMOS imager) (not shown). The light source 205 (e.g., lamp) is housed in a video processing unit 210 that processes signals that are input from the imager and outputs processed video signals to a video monitor (not shown) for viewing. The video processing unit 210 also serves as a component of an air/water feed circuit by housing a pressurizing pump 215, such as an air feed pump, in the unit.

The endoscope shaft 100a may include a distal tip 100c provided at the distal portion 100b of the shaft 100a and a flexible bending portion 105 proximal to the distal tip 100c. The flexible bending portion 105 may include an articulation joint (not shown) to assist with steering the distal tip 100c. On an end face 100d of the distal tip of the endoscope 100 is a gas/lens wash nozzle 220 for supplying gas to insufflate the interior of the patient at the treatment area and for supplying water to wash a lens covering the imager. An irrigation opening 225 in the end face 100d supplies irrigation fluid to the treatment area of the patient. Illumination windows (not shown) that convey illumination light to the treatment area, and an opening 230 to a working channel 235 extending along the shaft 100a for passing tools to the treatment area, also may be included on the face 100d of the distal tip 100c. The working channel 235 extends along the shaft 100a to a proximal channel opening 110 positioned distal to an operating handle 115 of the endoscope 100. A biopsy valve 120 may be utilized to seal the channel opening 110 against unwanted fluid egress.

The operating handle 115 may be provided with knobs 125 for providing remote 4-way steering of the distal tip via wires connected to the articulation joint in the bendable flexible portion 105 (e.g., one knob controls up-down steering and another knob control for left-right steering). A plurality of video switches 130 for remotely operating the video processing unit 210 may be arranged on a proximal end side of the handle 115. In addition, the handle is provided with dual valve wells 135 that receive a gas/water valve 140 for operating an insufflating gas and lens water feed operation. A gas supply line 240a and a lens wash supply line 245a run distally from the gas/water valve 140 along the shaft 100a and converge at the distal tip 100c proximal to the gas/wash nozzle 220 (FIG. 2). The other valve well 135 receives a suction valve 145 for operating a suction operation. A suction supply line 250a runs distally from the suction valve 145 along the shaft 100a to a junction point in fluid communication with the working channel 235 of the endoscope 100.

The operating handle 115 is electrically and fluidly connected to the video processing unit 210, via a flexible umbilical 260 and connector portion 265 extending therebetween. The flexible umbilical 260 has a gas (e.g., air or $CO_2$)

feed line 240b, a lens wash feed line 245b, a suction feed line 250b, an irrigation feed line 255b, a light guide (not shown), and an electrical signal cable. The connector portion 265 when plugged into the video processing unit 210 connects the light source 205 in the video processing unit with the light guide. The light guide runs along the umbilical 260 and the length of the endoscope shaft 100a to transmit light to the distal tip 100c of the endoscope 100. The connector portion 265 when plugged into the video processing unit 210 also connects the air pump 215 to the gas feed line 240b in the umbilical 260.

A water reservoir 270 (e.g., water bottle) is fluidly connected to the endoscope 100 through the connector portion 265 and the umbilical 260. A length of gas supply tubing 240c passes from one end positioned in an air gap 275 between the top 280 (e.g., bottle cap) of the reservoir 270 and the remaining water 285 in the reservoir to a detachable gas/lens wash connection 290 on the outside of the connector portion 265. The gas feed line 240b from the umbilical 260 branches in the connector portion 265 to fluidly communicate with the gas supply tubing 240c at the detachable gas/lens wash connection 290, as well as the air pump 215. A length of lens wash tubing 245c, with one end positioned at the bottom of the reservoir 270, passes through the top 280 of the reservoir to the same detachable connection 290 as the gas supply tubing 240c on the connector portion 265. In other embodiments, the connections may be separate and/or separated from each other. The connector portion 265 also has a detachable irrigation connection 293 for irrigation supply tubing (not shown) running from a source of irrigation water (not shown) to the irrigation feed line 255b in the umbilical 260. In some embodiments, irrigation water is supplied via a pump (e.g., peristaltic pump) from a water source independent (not shown) from the water reservoir 270. In other embodiments, the irrigation supply tubing and lens wash tubing 245c may source water from the same reservoir. The connector portion 265 may also include a detachable suction connection 291 for suction feed line 250b and suction supply line 250a fluidly connecting a vacuum source (e.g., hospital house suction) (not shown) to the umbilical 260 and endoscope 100.

The gas feed line 240b and lens wash feed line 245b are fluidly connected to the valve well 135 for the gas/water valve 140 and configured such that operation of the gas/water valve in the well controls supply of gas or lens wash to the distal tip 100c of the endoscope 100. The suction feed line 250b is fluidly connected to the valve well 135 for the suction valve 145 and configured such that operation of the suction valve in the well controls suction applied to the working channel 235 of the endoscope 100.

Referring to FIG. 2, an exemplary operation of an endoscopic system 200, including an endoscope such as endoscope 100 above, is explained. Air from the air pump 215 in the video processing unit 210 is flowed through the connection portion 265 and branched to the gas/water valve 140 on the operating handle 115 through the gas feed line 240b in the umbilical 260, as well as through the gas supply tubing 240c to the water reservoir 270 via the connection 290 on the connector portion 265. When the gas/water valve 140 is in a neutral position, without the user's finger on the valve, air is allowed to flow out of the valve to atmosphere. In a first position, the user's finger is used to block the vent to atmosphere. Gas is allowed to flow from the valve 140 down the gas supply line 240a and out the distal tip 100c of the endoscope 100 in order to, for example, insufflate the treatment area of the patient. When the gas/water valve 140 is pressed downward to a second position, gas is blocked from exiting the valve, allowing pressure of the air passing from the air pump 215 to rise in the water reservoir 270. Pressurizing the water source forces water out of the lens wash tubing 245c, through the connector portion 265, umbilical 260, through the gas/water valve 140 and down the lens wash supply line 245a, converging with the gas supply line 240a prior to exiting the distal tip 100c of the endoscope 100 via the gas/lens wash nozzle 220. Air pump pressure may be calibrated to provide lens wash water at a relatively low flow rate compared to the supply of irrigation water.

The volume of the flow rate of the lens wash is governed by gas pressure in the water reservoir 270. When gas pressure begins to drop in the water reservoir 270, as water is pushed out of the reservoir 270 through the lens wash tubing 245c, the air pump 215 replaces lost air supply in the reservoir 270 to maintain a substantially constant pressure, which in turn provides for a substantially constant lens wash flow rate. In some embodiments, a filter (not shown) may be placed in the path of the gas supply tubing 240c to filter-out undesired contaminants or particulates from passing into the water reservoir 270. In some embodiments, outflow check valves or other one-way valve configurations (not shown) may be placed in the path of the lens wash supply tubing to help prevent water from back-flowing into the reservoir 270 after the water has passed the valve.

A relatively higher flow rate compared to lens wash is typically required for irrigation water, since a primary use is to clear the treatment area in the patient of debris that obstructs the user's field of view. Irrigation is typically achieved with the use of a pump (e.g., peristaltic pump), as described. In embodiments with an independent water source for irrigation, tubing placed in the bottom of a water source is passed through the top of the water source and threaded through the head on the upstream side of the pump. Tubing on the downstream side of the pump 255c is connected to the irrigation feed line 255b in the umbilical 260 and the irrigation supply line 255a endoscope 100 via the irrigation connection 293 on the connector portion 265. When irrigation water is required, fluid is pumped from the water source by operating the irrigation pump, such as by depressing a footswitch (not shown), and flows through the irrigation connection 293, through the irrigation feed line 255b in the umbilical, and down the irrigation supply line in the shaft 100a of the endoscope to the distal tip 100c. In order to equalize the pressure in the water source as water is pumped out of the irrigation supply tubing, an air vent (not shown) may be included in the top 280 of the water reservoir 270. The vent allows atmospheric air into the water source preventing negative pressure build-up in the water source, which could create a vacuum that suctions undesired matter from the patient back through the endoscope toward the water source. In some embodiments, outflow check valves or other one-way valve configurations (not shown), similar to the lens wash tubing 245c, may be placed in the path of the irrigation supply tubing to help prevent back-flow into the reservoir after water has passed the valve.

FIGS. 3A-3D are schematic drawings illustrating the operation of an embodiment of a hybrid system 300 where the supply tubing for irrigation and lens wash are connected to and drawn from a single water reservoir. The hybrid system 300 includes the single water reservoir 305, a cap 310 for the reservoir, gas supply tubing 240c, lens wash supply tubing 245c, irrigation pump 315 with foot switch 318, upstream irrigation tubing 320 and downstream irrigation supply tubing 255c. The cap 310 may be configured to attach in a seal-tight manner to the water reservoir 305 by a typically threaded arrangement. The cap may include a gasket to seal the cap 310 to the reservoir 305. The gasket can be an O-ring, flange, collar, and/or the like and can be formed of any suitable material. A number of through-openings (325a, 325b, 325c) in the cap 310 are provided to receive, respectively, the gas supply tubing 240c, lens wash supply tubing 245c, and upstream irrigation supply tubing 320. In FIGS. 3A-3D, the system depicted includes separate tubing for gas supply, lens wash and irrigation.

In other embodiments, the gas supply tubing 240c and lens wash tubing 245c may be combined in a coaxial arrangement, as will be described in more detail below, such as with respect to FIGS. 11A-11C, and 14A-14B. For example, the gas supply tubing may define a lumen that is sufficiently large in diameter to encompass a smaller diameter lens wash tubing, coaxially received within the gas supply tubing, as well as provide air to the water source in an annular space surrounding the lens wash tubing to pressurize the water reservoir (see, e.g., gas and lens wash supply tubing 240c, 245c). The lens wash supply tubing may be configured to exit the lumen defined by the coaxial gas supply tubing in any suitable sealed manner, such as, for example, an aperture, fitting, collar, and/or the like, for the purpose of transitioning from the coaxial arrangement to a side-by-side arrangement at the detachable gas/lens wash connection to the endoscope connector portion (e.g., connector portion 265 of FIG. 2).

In various embodiments, different configurations of valving (not shown) may be incorporated into various embodiments disclosed hereby, including the tubing of the system 200, 300. For example, an in-flow check valve can be disposed in the path of the gas supply tubing 240c to help prevent backflow into the air pump 215. In this manner, pressure building within the water reservoir 270, 305 creates a pressure difference between the water source and the gas supply tubing 240c helping to maintain a positive pressure in the water source even when large amounts of water may be removed from the water source during the irrigation function. This arrangement compensates for any time lag in air being delivered from the air pump 215 to the water reservoir 270, 305, which might otherwise cause a negative pressure vacuum in the water reservoir. Similarly, an outflow check valve, such as the one-way valve with inlet/outlets and valve insert, may be incorporated in the lens wash supply tubing 240c, upstream irrigation supply tubing 320, and/or downstream irrigation supply tubing 255c to help prevent backflow of water from either or both of the lens wash and irrigation tubing in the event of a negative pressure situation, as described. One or more of these techniques are described in more detail below, such as with respect to FIGS. 14A and 14B.

More generally, in many embodiments, a check valve may refer to any type of configuration for fluid to flow only in one direction in a passive manner. For example, a check valve may include, or refer to, one or more of a ball check valve, a diaphragm check valve, a swing check valve, a tilting disc check valve, a flapper valve, a stop-check valve, a lift-check valve, an in-line check valve, a duckbill valve, a pneumatic non-return valve, a reed valve, a flow check. Accordingly, a check valve as used herein is meant to be separate and distinct from an active valve that is operated in a binary manner as an on/off valve or switch to allowed flow to be turned on or allow flow to be turned off (e.g., a stop cock valve, solenoid valve, peristaltic pump).

During operation of the system of FIGS. 3A-3D, a flow of water for irrigation may be achieved by operating the irrigation pump 315. A flow of water for lens wash may be achieved by depressing the gas/water valve 140 on the operating handle 115 of the endoscope 100. These functions may be performed independent of one another or simultaneously. When operating lens wash and irrigation at the same time, as fluid is removed from the water reservoir 270, 305, the pressure in the system may be controlled to maintain the lens wash supply tubing 240c at substantially the pressure necessary to accomplish a lower flow rate lens wash, while compensating for reduced pressure in the water reservoir 270, 305 due to supplying a high flow rate irrigation. When pressure is reduced in the water reservoir by use of the lens wash function, the irrigation function, or both functions simultaneously, the reduced pressure may be compensated for by the air pump 215 via the gas supply tubing 240c.

Figure 3A:
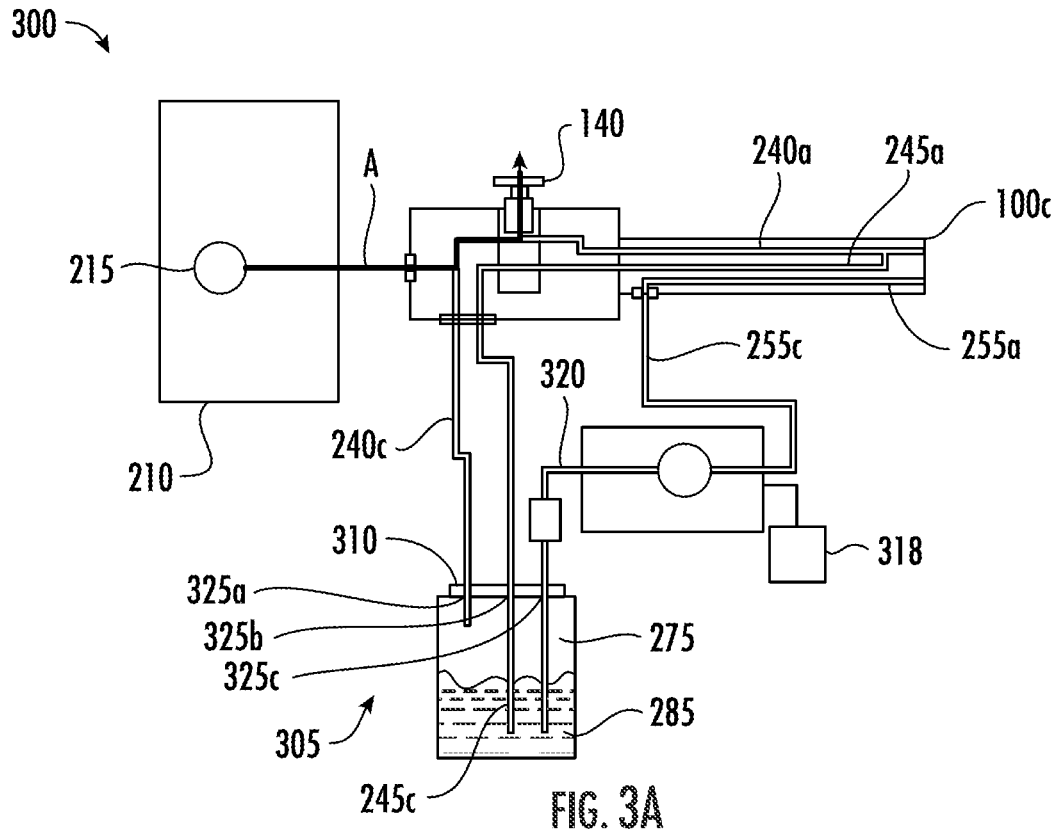
FIG. 3A depicts an endoscope system with endoscope, light source, water reservoir, and tubing assembly for hybrid air, lens wash and irrigation fluid delivery, wherein the system is activated to deliver air to atmosphere.

The schematic set-up in FIGS. 3A-3D has been highlighted to show the different flow paths possible with the hybrid system 300 having supply tubing for irrigation 320 and lens wash 240c connected to and drawn from the single water reservoir 305. As shown in FIG. 3A, the endoscope 100 is in a neutral state with the gas/water valve 140 in an open position. The neutral state delivers neither gas, nor lens wash, to the distal tip of the endoscope. Rather gas (pressure) is delivered along path A from the pressurizing air pump 215 and vented through the gas feed line 240b in the umbilical 260 via the connector portion 265 and through the gas/water valve to atmosphere. Since the system is open at the vent hole in the gas/water valve 140, there is no build up to pressurize the water reservoir 305 and consequently no water is pushed through the lens wash supply tubing 240c.

Figure 3B:
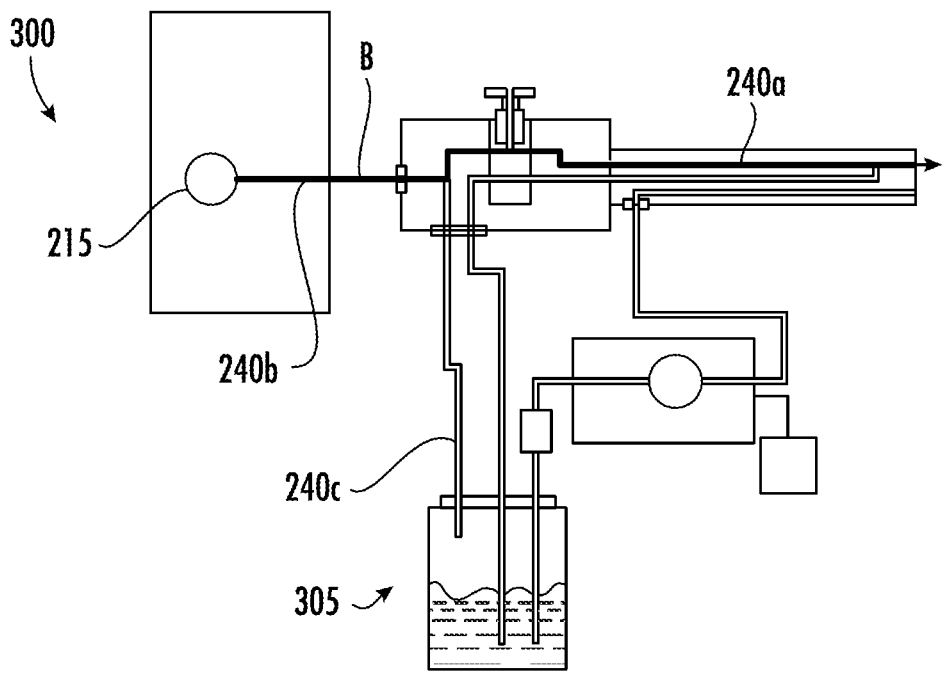
FIG. 3B depicts the endoscope system of FIG. 3A, wherein the system is activated to deliver air to a patient through the patient end of the endoscope.

As shown in FIG. 3B, the endoscope 100 is in a gas delivery state with the gas/water valve 140 in a first position. When gas is called for at the distal tip 100c, for example, to clean the end face 100d of the distal tip or insufflate the patient body in the treatment area, the user closes off the vent hole in the gas/water valve 140 with a thumb, finger, or the like (first position). In this state, gas (pressure) is delivered along path B from the air pump 215 and flowed through the gas feed line 240b in the umbilical 260 via the connector portion 265. The gas continues through the gas/water valve 140 to the gas supply line 240a in the endoscope shaft 100a and out the gas/lens wash nozzle 220 at the distal tip 100c. There is no build up to pressurize the water reservoir since the system is open at the gas/lens water nozzle 220, and consequently no water is pushed through the lens wash supply tubing 240c.

Figure 3C:
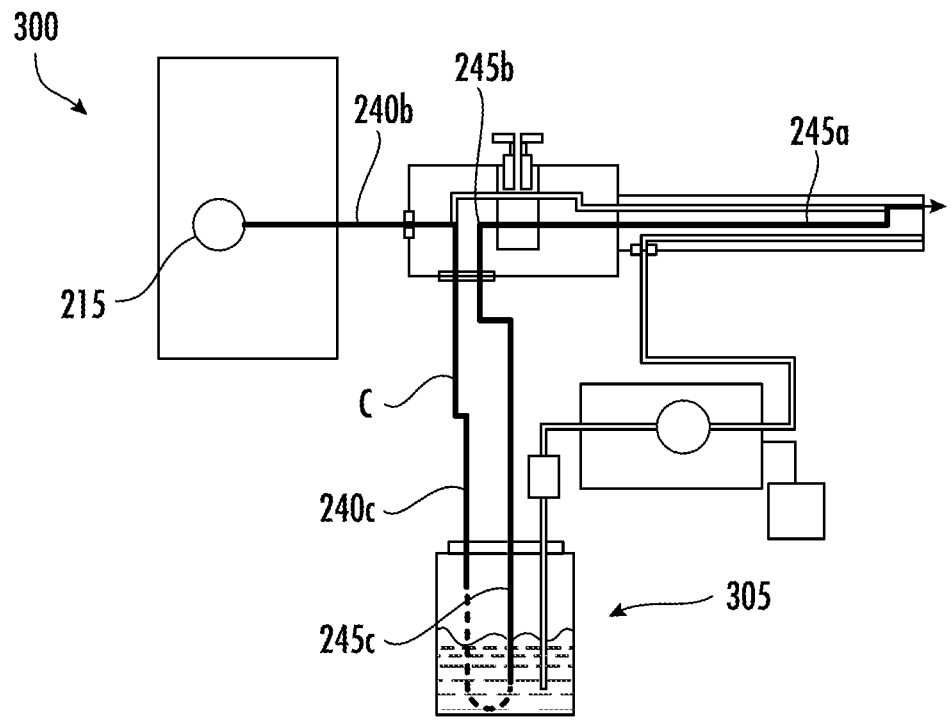
FIG. 3C depicts the endoscope system of FIG. 3A, wherein the system is activated to deliver lens wash fluid through the patient end of the endoscope.

As shown in FIG. 3C, the endoscope 100 is in a lens wash delivery state with the gas/water valve 140 in a second position. When lens wash is called for at the distal tip 100c, for example, to clean the end face 100d of the distal tip 100c, the user, keeping the vent hole in the air/water valve closed off, depresses the valve 140 to its furthest point in the valve well 135. The second position blocks off the gas supply to both atmosphere and the gas supply line 240a in the endoscope, and opens up the gas/water valve 140 to allow lens wash water to pass through to the lens wash supply line 245a in the endoscope shaft 100a and out the gas/lens wash nozzle 220 at the distal tip 100c. In this state, gas (pressure) is delivered along path C from the air pump 215, through the branched line in the connector portion 265 and out of the gas supply tubing 240c to the water reservoir 305. The gas (pressure) pressurizes the surface of the remaining water 285 in the reservoir 305 and pushes water up the lens wash supply tube 245c to the connector portion 265. The pressurized lens wash water is pushed further through the lens wash feed line 245b in the umbilical 260 and through the gas/water valve 140. Since the system 300 is closed, gas pressure is allowed to build and maintain a calibrated pressure level in the water reservoir 305, rather than venting to atmosphere or being delivered to the patient. This pressure, along with the endoscope feed and supply lines and external tubing, translates to a certain range of flow rate of the lens wash.

Figure 3D:
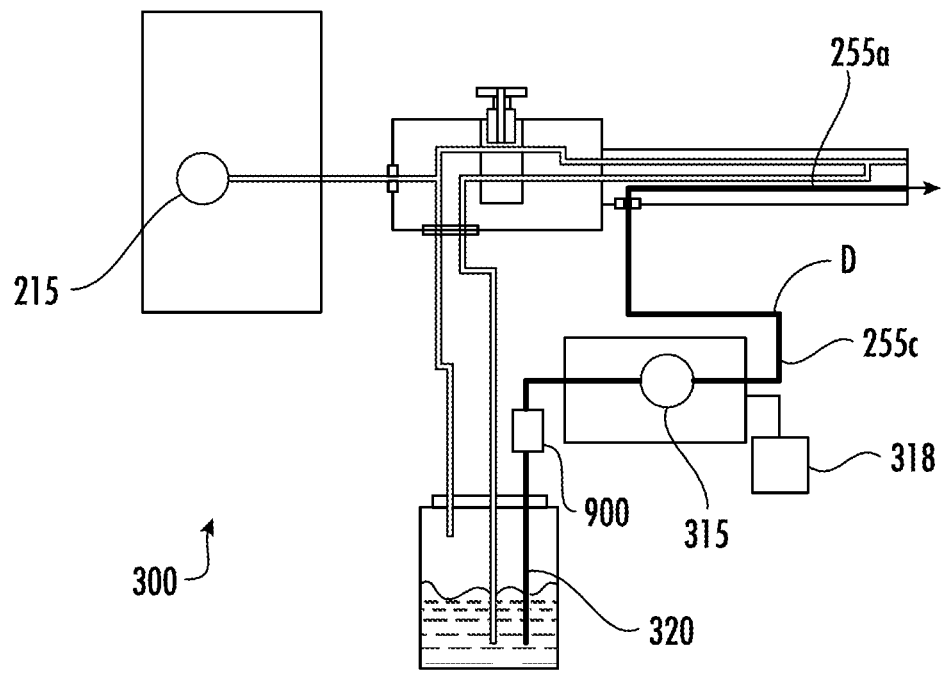
FIG. 3D depicts the endoscope system of FIG. 3A, wherein the system is activated to deliver irrigation fluid through the patient end of the endoscope.

As shown in FIG. 3D, the endoscope 100 is in an irrigation delivery state. This may be performed at the same or a different time from the delivery of gas and/or lens wash. When irrigation is called for at the distal tip 100c, for example, if visibility in the treatment area is poor or blocked by debris, or the like, the user activates the irrigation pump 315 (e.g., by depressing foot switch 318) to delivery water along path D. With the pump 315 activated, water is sucked out of the water reservoir 305 through the upstream irrigation supply tubing 320 and pumped along the downstream irrigation supply tubing 255c to the connector portion 265. The irrigation pump head pressure pushes the irrigation water further through the irrigation feed line 255b in the umbilical 260, through the irrigation supply line 255a in the endoscope shaft 100a, and out the irrigation opening 225 at the distal tip 100c. The irrigation pump pressure may be calibrated, along with the endoscope irrigation feed and supply lines and external tubing, to deliver a certain range of flow rate of the irrigation fluid.

Figure 4:
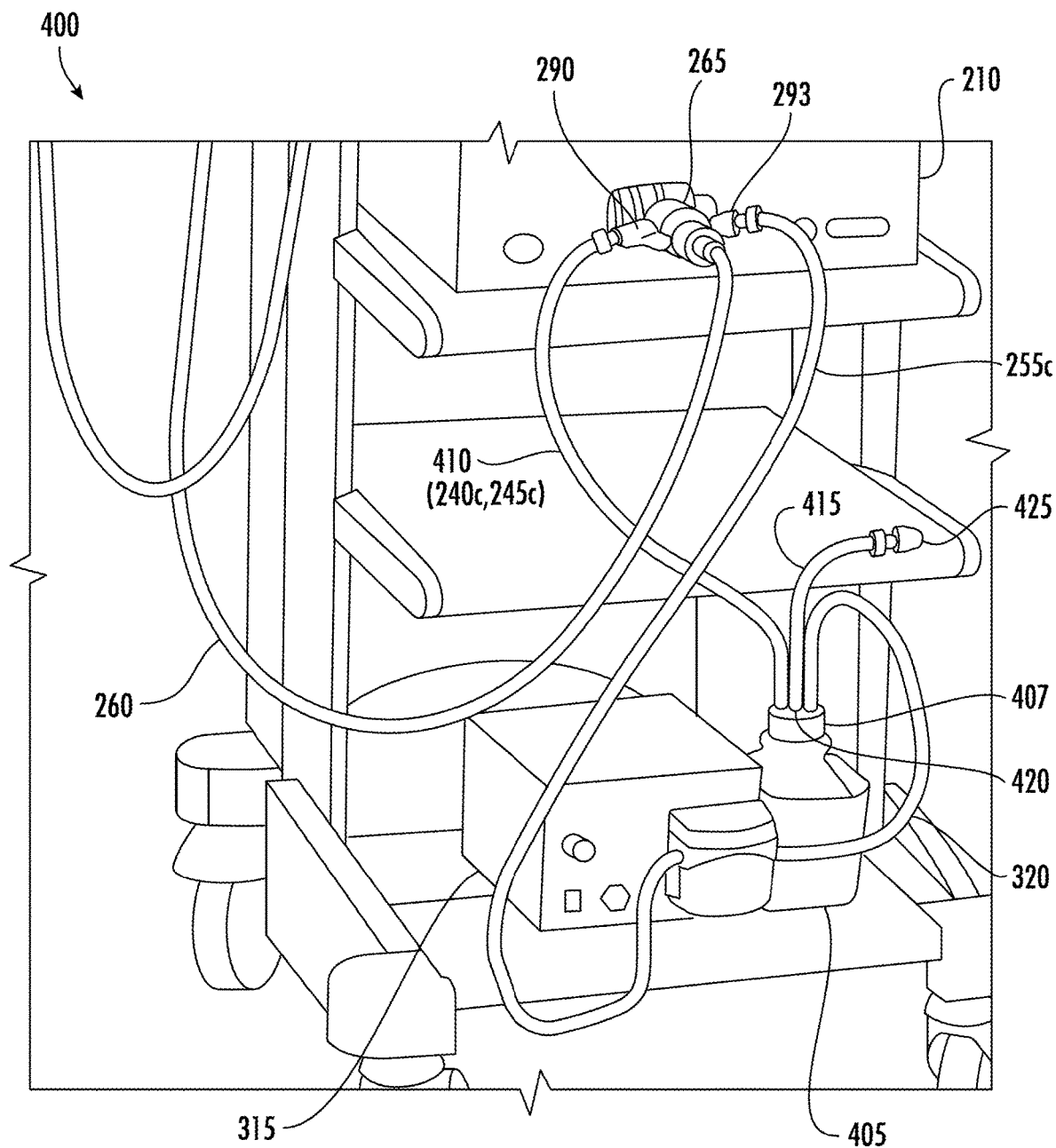
FIG. 4 depicts an endoscope system with endoscope, light source, water reservoir, and tubing assembly for hybrid air/lens wash, irrigation, and gas fluid delivery.

FIG. 4 is a schematic drawing illustrating a further embodiment of a hybrid system 400 including a video processing unit 210, connector portion 265, peristaltic irrigation pump 315, water reservoir 405 and top 407, coaxial gas and lens wash supply tubing 410, upstream and downstream irrigation supply tubing 320, 255c, and alternative gas supply tubing 415 (e.g., $CO_2$). A length of the alternative gas supply tubing 415 passes from one end positioned in the gas gap 275 between the top 407 of the water reservoir 405 and the remaining water 285 in the reservoir through an additional opening 420 in the top of the reservoir to a detachable connection 425 for a source of the alternative gas supply (e.g., $CO_2$ hospital house gas source). When the alternative gas supply is desired, such as $CO_2$ gas, the air pump 215 on the video processing unit 210 may be turned off and $CO_2$ gas, rather than air, is thereby flowed to the water reservoir 405 pressurizing the water surface. In the neutral state, $CO_2$ gas flows backward up the gas supply tubing 240c to the connector portion 265, up the gas feed line 240b, and is vented through the gas/water valve 140 to atmosphere. In the first position, the user closes off the vent hole in the gas/water valve 140, and the $CO_2$ gas is flowed through the gas/water valve to the gas supply line 240a in the endoscope shaft 100a and out the gas/lens wash nozzle 220 at the distal tip 100c. In the second position, the user depresses the valve 140 to the bottom of the valve well 135, keeping the vent hole in the gas/water valve closed off. The second position blocks the $CO_2$ gas supply to both atmosphere and the gas supply line 240a in the endoscope 100, and opens up the gas/water valve 140 to allow lens wash water to pass through to the lens wash supply line 245a in the endoscope shaft 100a and out the gas/lens wash nozzle 220 at the distal tip 100c. Gas (pressure) in the reservoir 405 is maintained by delivery gas through alternative gas (e.g., $CO_2$) supply tubing 415. The irrigation function may be accomplished in a similar manner as the operation described above with respect to FIG. 3D.

Referring to FIGS. 5-11C and 14-15 in accordance with principles of the present disclosure, in one embodiment, the water reservoir, bottle, container, etc. (such terms being used interchangeably without intent to limit or otherwise convey different meaning or intent) and the tubing assembly or tube sets (such terms being used interchangeably without intent to limit or otherwise convey different meaning or intent) may be integrally formed so that the water container and one or more tubes are permanently and non-separably coupled to each other (e.g., tubes are incapable of being disconnected from the container (e.g., cap of existing devices is eliminated). Collectively referred to herein as an integrated container and tube set. It will be appreciated that one or more tubes of an integrated container and tube set may be removably coupled to the container without departing from the scope of this disclosure.

In embodiments formed in accordance with principles of the present disclosure, container and tube sets are combined into an integrated container and tube set in which one or more of the tubes are combined or merged with the container, which is filled with a fluid such as, $H_2O$, and air such as, for example, air, $CO_2$, etc. For example, in one embodiment, the container and the tubes may be simultaneously formed or molded. Alternatively, in one embodiment, the tubes may be initially formed or molded and the container may be formed or molded around, to, or the like, the tubes. The integrated container and tube set may then be filled with water and sealed to create a sterilized container for use in an endoscopic procedure. Thus arranged, an improved fluid and gas container is provided that decreases the likelihood of infection. In addition, the integrated container and tube set provides manufacturers with increased flexibility and fewer component parts. In one embodiment, the integrated container and tube set can be configured as a single use item (e.g., a disposable single use item that is intended to be discarded after use), although, in one embodiment, the integrated container and tube set can be refillable and thus reusable. In one embodiment, the integrated container and tube set may be provided in an off-the-shelf sterile container to supply fluid and/or gases to an endoscope during an endoscopic procedure.

In one embodiment, the integrated container and tube set may replace (e.g., take the place of) the water reservoir and cap of the system described above in connection with FIGS. 1-4. That is, during use, the integrated container and tube set may be used in conjunction with (e.g., coupled to) an endoscope to supply fluid and/or gases to the endoscope in order to, for example, irrigate, lens wash, and insufflate during the endoscopic procedure. To this end, in one embodiment, the integrated water reservoir and tube set includes a plurality of tubes (e.g., lumens) for suppling fluid (e.g., water) and/or gas (e.g., $CO_2$, air, etc.) to an endoscope to accommodate various endoscopic procedures as previously described. For example, in one embodiment, the integrated container and tube set may include a first irrigation supply tube, a second lens wash supply tube, and a third gas supply tube. In addition, the integrated container and tube set may include a fourth alternate gas supply tube. Thus arranged, as previously described above in connection with FIGS. 1-4, depending on actuation of the endoscope system, the integrated container and tube set may be arranged and configured to (i) supply gas (e.g., air or $CO_2$) to insufflate the patient, (ii) supply fluid to flush or clean the lens of the endoscope, and (iii) supply fluid for irrigation (e.g., flushing and/or suctioning of the working channel). During use, as previously described above in connection with FIGS. 1-4, depending on the user's manipulation of the valves on the endoscopes and other corresponding foot pedals and connectors, delivery of either fluid or gas to the endoscope in a desired manner is provided (e.g., supplying high pressure/volume fluid for irrigation, fluid for lens wash, or air/gas for patient insufflation.

In many embodiments formed in accordance with principles of the present disclosure, aspects of the present disclosure may result in more efficient and/or environmentally friendly endoscopic systems. In several embodiments, the integrated container and tube sets may reduce waste, such as by facilitating reusability. For example, fill ports may be included to replenish a supply of liquid in the containers. The fill ports may additionally enable the use of different fluids, such as to support a multitude of endoscopic procedures. In some embodiments, the integrated container and tube sets may decrease associated logistical and storage costs. For example, the integrated container may be collapsible to reduce volume needed to store or package the integrated container and tube sets. In various embodiments, the integrated container and tube sets may reduce manufacturing complexity. For example, integrally forming one or more components can reduce assembly steps. In many embodiments, the integrated container and tube sets may include containers with one or more interfaces configured to enable the container to be used in conjunction with a variety of systems and configurations. In various embodiments, components of the integrated container and tube sets may include features to reduce cleaning and/or processing time, such as between procedures. For example, coaxial tubing may reduce the amount of surface area that must be cleaned. Additionally, or alternatively, the integrated container and tube sets may include containers designed and shaped to promote efficiency and adaptability. For example, the containers may include features, such as a neck portion at gas tubing connection ports, to reduce, or prevent, flow of liquid into gas tubing. In another example, the containers may be designed such that irrigation supply tubing is coupled at the lower point of the reservoir, such as to promote the flow of liquid from the container to the irrigation supply tube.

In addition, and/or alternatively, in one embodiment, each of the tubes may be sealed to maintain a sterile environment prior to use (e.g., container and tubes are sealed). In addition, and/or alternatively, each of the tubes may include, for example, a one-way valve, to prevent backflow into the container during use. For example, in one embodiment, each of the tubes may include a one-way valve in the second end of the tube to prevent backflow of fluid into the container during use. In addition, and/or alternatively, one or more of the tubes may include a connector or adapter such as, for example, a Tuohy Borst connector, an adjustable connector such as, for example, stop-cock adaptor, a split connector such as, for example, a coaxial split connector or scope adapter arranged and configured to couple to the endoscope, etc. In use, the adapters may be arranged and configured in a normally closed position to maintain the sterile environment prior to use. Thereafter, during use, as needed, the user can move one or more of the adapters from the closed position to an opened position to enable flow of fluid and/or gas as needed.

Figure 5:
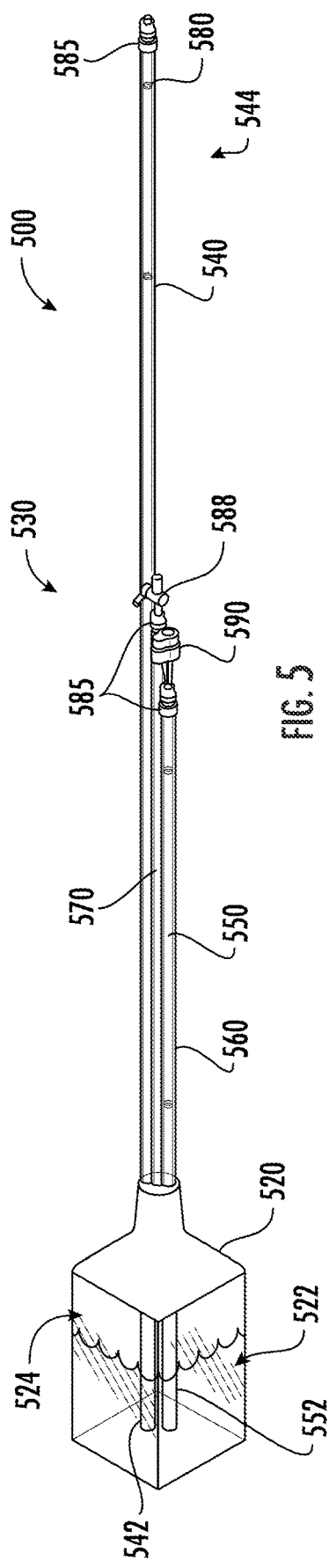
FIG. 5 depicts an integrated container and tube set or assembly suitable for use with an endoscope system, according to an embodiment of the present disclosure.
Figure 6:
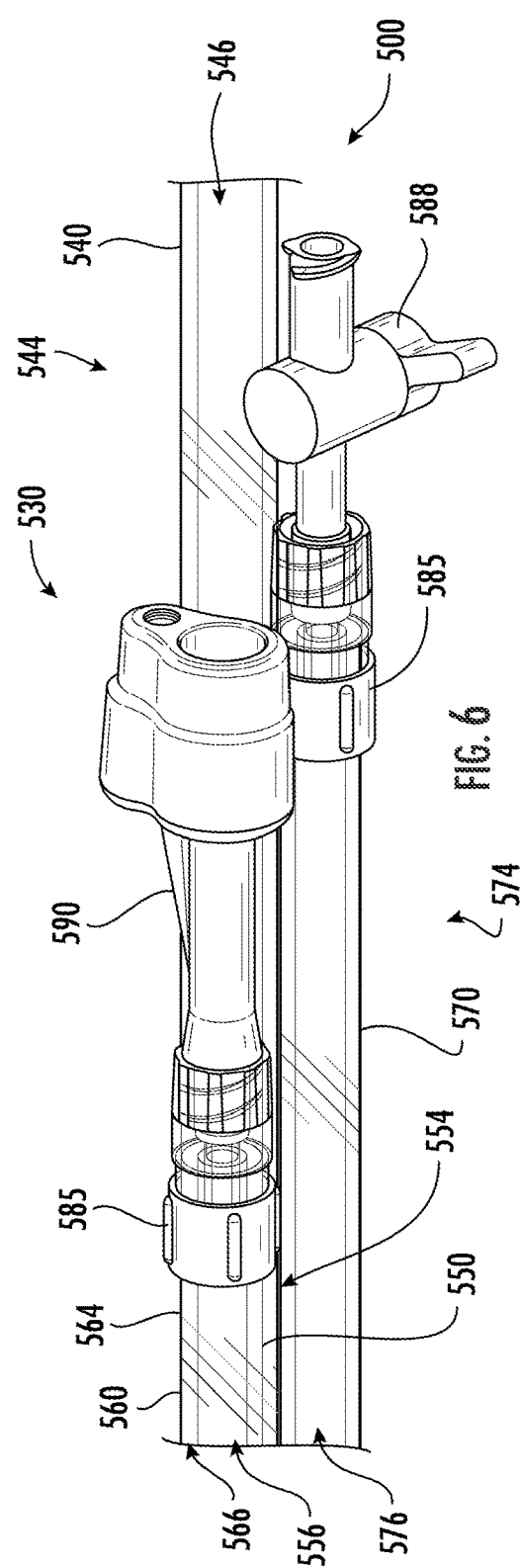
FIG. 6 depicts a detailed view of a second end of the tubes of the integrated container and tube set of FIG. 5, wherein one or more of the tubes include a one-way valve and/or an adaptor (e.g., a coaxial split connector, a stop-cock adaptor), according to an embodiment of the present disclosure.
Figure 7:
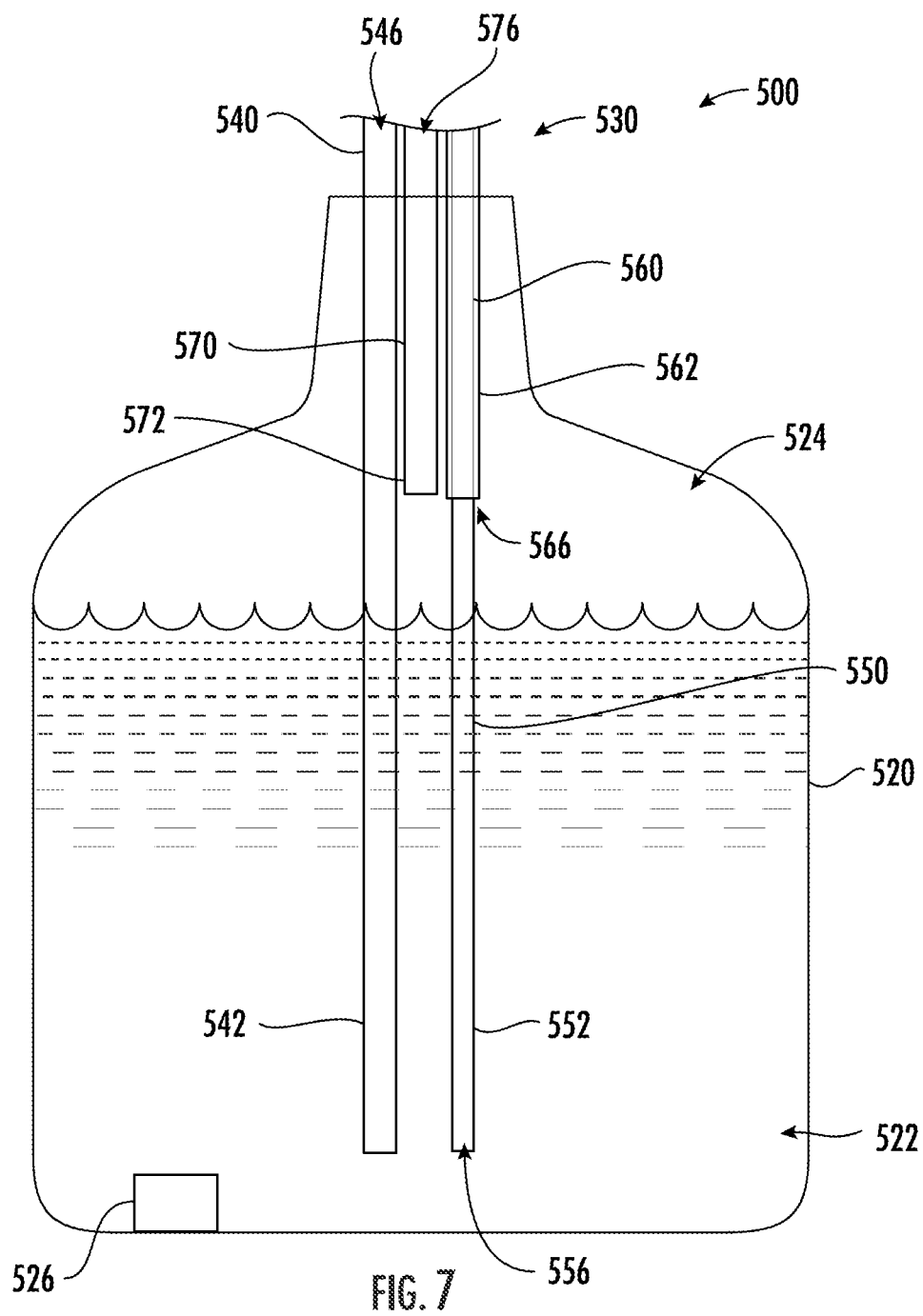
FIG. 7 depicts a cross-sectional view of the integrated container and tube set of FIG. 5, wherein the first and second tubes are in fluid communication with a bottom portion of the container and the third and fourth tubes are in communication with a top portion of the container, according to an embodiment of the present disclosure.

Turning now to the FIGURES, various embodiments of an integrated container and tube set are illustrated for the sake of disclosing and describing informative examples without intent to limit the disclosure from the broad principles described herein. FIGS. 5-7 illustrate an embodiment of an integrated container and tube set 500 formed in accordance with various principles of the present disclosure. As previously mentioned, the integrated container and tube set 500 may be used in place of the water reservoir 270 (e.g., water bottle) described above in connection with FIGS. 1-4. As illustrated in FIGS. 5-7, the integrated container and tube set 500 includes a container (e.g., a water bottle, reservoir, etc.) 520 and a plurality of tubes 530 associated with the container 520. In one embodiment, each of the plurality of tubes 530 includes an outer wall that is continuous with the container 520. That is, the plurality of tubes 530 may be integrally formed with the container 520 (e.g., tubes 530 may be permanently and non-separably molded to the container 520 so that there is no interconnecting removable cap between the tubes and the container such as, for example, cap or top 280, 310).

In one embodiment, as illustrated, the container 520 may be arranged and configured as a rigid (e.g., non-compressible) container manufactured from any suitable material now known or hereafter developed including, for example, a plastic, an elastomer, or the like. As illustrated, the container 520 may have a generally rectangular shape, although this is but one configuration and the container 520 may have other shapes such as, for example, square, cylindrical, or the like. The container 520 includes a bottom portion 522 arranged and configured to hold, receive, store, etc. a fluid such as, for example, $H_2O$, and a top portion (e.g., an air gap) 524 arranged and configured to hold, receive, store, etc. a gas such as, for example, air, $CO_2$, etc. so that, depending on operation of the endoscope as previously described including, for example, the user's actuation of the endoscopic valves and/or foot petals, fluid or gas can be supplied to the endoscope as needed.

In accordance with aspects of the present disclosure, and as previously mentioned, the tubes 530 may be integrally formed with the container 520 so that the container 520 and tubes 530 can be provided as a single fluid delivery device. The integrated container and tube set 500 may be integrally formed by any suitable method now known or hereafter developed. For example, in one embodiment, the tubes 530 may be formed at the same time as the container 520 using, for example, moldable plastic, elastomer, or the like. For example, the container 520 may be molded to each of the plurality of tubes 530. Alternatively, the tubes 530 may be initially formed and then the container 520 may be molded around the pre-existing tubes 530 creating the integral assembly. In this manner, the tubes 530 may be manufactured from a different material than the container 520.

In either event, once properly manufactured, the integrated container and tube set 500 may be filled with a fluid such as, for example, $H_2O$, in the bottom portion thereof 522 and a gas such as, for example, air, in the top portion 524 thereof. The integrated container and tube set 500 may then be subsequently sealed or capped. In one embodiment, the container 520 may be filled using one or more of the integrated tubes 530 (e.g., the fluid and/or gas may be inserted into the container 520 through the second end of the integrated tubes 530). Alternatively, in one embodiment, the container 520 may include a supply port 526 (FIG. 3) for injecting the fluid therein. That is, in one embodiment, the container 520 may include a supply port 526 such as, for example, in a bottom surface thereof, arranged and configured to couple with a fluid supply to supply fluid into the container 520. In either event, thereafter, the integrated container and tube set 500 may be sealed or cap and then sterilized creating a sealed, integrated sterile container and tube set 500 (e.g., fluid is sealed from the surrounding atmosphere). That is, as will be described in greater detail below, each of the tubes 530 may be sealed or capped to prevent air or the like from entering into the integrated container and tube set 500.

As previously mentioned, the integrated container and tube set 500 may include a plurality of tubes 530. For example, referring to FIGS. 5 and 7, in one embodiment, the integrated container and tube set 500 may include first, second, third, and fourth tubes 540, 550, 560, 570, although this is but one configuration and more or less tubes may be provided such as, for example, one, two, three, etc. depending on the medical procedure being performed. As illustrated, the first tube 540 may include a first end 542, a second end 544, and a first lumen 546 extending from the first end 542 to the second end 544. As previously mentioned, in one embodiment, the first tube 540 is integrally formed with the container 520 (e.g., the first tube 540 includes an outer wall that is continuous with the container 520). With the first tube 540 passing through the container 520, the first end 542 of the first tube 540 is arranged and configured in fluid communication with the bottom portion 522 of the container 520 while the second end 544 of the first tube 540 is arranged and configured to extend external from the container 520 so that the second end 544 is positioned external to the container 520. Thus arranged, the first tube 540 is arranged and configured to supply fluid to the endoscope. In one embodiment, as previously described above in connection with FIGS. 1-4, the first tube 540 may be arranged and configured to be operatively coupled to a pump (e.g., peristaltic pump) so that fluid can be sucked from the container 520 to provide irrigation (e.g., lower pressure, higher volume water may be provided by utilizing a pump to suck water from the container 520). That is, the second end 544 of the first tube 540 may be operatively coupled to a pump (e.g., peristaltic pump) so that the first lumen 546 is arranged and configured to fluidly couple to an irrigation channel of the endoscope for supplying fluid (e.g., $H_2O$) from the container 520 to the irrigation channel of the endoscope as needed. In this manner, the first tube 540 may also be referred to as an irrigation supply tube.

In one embodiment, the integrated container and tube set 500 may also include a second tube 550 including a first end 552, a second end 554, and a second lumen 556 extending from the first end 552 to the second end 554. As previously mentioned, in one embodiment, the second tube 550 is integrally formed with the container 520 (e.g., the second tube 550 includes an outer wall that is continuous with the container 520). With the second tube 550 passing through the container 520, the first end 552 of the second tube 550 is arranged and configured in fluid communication with the bottom portion 522 of the container 520 while the second end 554 of the second tube 550 is configured to extend external from the container 520 so that the second end 554 of the second tube 550 is positioned external to the container 520. Thus arranged, the second tube 550 is arranged and configured to supply fluid to the endoscope. In one embodiment, as previously described above in connection with FIGS. 1-4, depending on actuation of the various valves on the endoscope by the surgeon, the second tube 550 may be arranged and configured to wash, clean, or the like, the lens of the endoscope (e.g., to provide fluid across an imaging lens of the endoscope). In this manner, the second tube 550 may also be referred to as a lens wash supply tube.

In one embodiment, the integrated container and tube set 500 may also include a third tube 560 including a first end 562, a second end 564, and a third lumen 566 extending from the first end 562 to the second end 564. As previously mentioned, in one embodiment, the third tube 560 is integrally formed with the container 520 (e.g., the third tube 560 includes an outer wall that is continuous with the container 520). With the third tube 560 passing through the container 520, the first end 562 of the third tube 560 is arranged and configured in operatively communication with the top portion 524 of the container 520 while the second end 564 of the third tube 560 is arranged and configured to extend external from the container 520 so that the second end 564 is positioned external to the container 520. Thus arranged, the third tube 560 is arranged and configured to supply air to the endoscope. For example, in one embodiment, as previously described above in connection with FIGS. 1-4, the third tube 560 may be operatively coupled to a pump (e.g., an air pump). In one embodiment, the third tube 560 may be arranged and configured to work in conjunction with the second tube 550. That is, depending on, inter alia, actuation of the valves on the endoscope by the surgeon, air may be supplied from the pump to the container 520 via the third tube 560 to pressurize the container 520 to push fluid through the second lumen 550 to lens wash. Alternatively, depending on, inter alia, actuation of the valves on the endoscope by the surgeon, air may be supplied from the pump via the third tube 560 to the endoscope to insufflate the patient with air. Thus, in one configuration, in use, the second and third tubes 550, 560 (e.g., second and third lumens 556, 566) may be utilized to pressurize the container 520 with air to supply fluid ($H_2O$) to the endoscope for cleaning the lens (e.g., lens wash). Alternatively, in another configuration, in use, the third tube 560 (e.g., third lumen 566) may be utilized to supply air to the patient for insufflation. Thus arranged, the third tube 560 may be referred to as a gas supply tube.

In one embodiment, as best illustrated in FIG. 7, the second or lens wash supply tube 550 and the third or gas supply tube 560 (e.g., second and third lumens 556, 566) may be combined into a single, multi-lumen tube. Thus arranged, in one embodiment, the second lumen 556 may be coaxial with the third lumen 566. For example, the second lumen 556 may be disposed or positioned within the third lumen 566. Alternatively, however, the second and third lumens 556, 566 may be disposed adjacent to each other in, for example, a side-by-side relationship. For example, in one embodiment, the multi-lumen tube may include an internal wall extending along a length thereof between the second lumen 556 and the third lumen 566.

Thus arranged, the second lumen 556 is arranged and configured to extend from the second end of the multi-lumen tube to the first end of the multi-lumen tube so that the second lumen 556 is arranged and configured to be in fluid communication with the bottom portion 522 of the container 520. The third lumen 566 is arranged and configured to extend from the second end of the multi-lumen tube towards the first end of the multi-lumen tube. However, the third lumen 566 is arranged and configured to be in operatively communication with the top portion 524 of the container 520 (e.g., the third lumen 566 does not extend as far longitudinally into the container 520 as the second lumen 556).

With continued reference to FIGS. 5-7, in one embodiment, the integrated container and tube set 500 may also include a fourth tube 570 having a first end 572, a second end 574, and a fourth lumen 576 extending from the first end 572 to the second end 574. As previously mentioned, in one embodiment, the fourth tube 570 is integrally formed with the container 520 (e.g., the fourth tube 570 includes an outer wall that is continuous with the container 520). With the fourth tube 570 passing through the container 520, the first end 572 of the fourth tube 570 is arranged and configured in operative communication with the top portion 524 of the container 520 while the second end 574 of the fourth tube 570 is arranged and configured to extend external from the container 520 so that the second end 574 is positioned external to the container 520.

In use, in one embodiment and as previously described above in connection with FIGS. 1-4, the fourth lumen 576 may be arranged and configured to work in conjunction with the third lumen 566. For example, in one embodiment, with the pump coupled to the gas supply tube 560 turned off, the fourth lumen 576 may be operatively coupled to a gas source such as, for example, a $CO_2$ source. Thereafter, with the air pump turned off, $CO_2$ may be supplied from the $CO_2$ source into the container 520 via the fourth tube 570 to pressurize the container 520 with $CO_2$ which may then be supplied to the endoscope via the gas supply tube 560 to insufflate the patient with $CO_2$ by passing the $CO_2$ through the endoscope in a controlled manner into the target space (e.g., with the pump coupled to the gas supply tube 560 in the off position, $CO_2$ may be supplied from the $CO_2$ source to the container 520 via the fourth tube 570, which causes the container 520 to pressurize resulting in $CO_2$ being supplied to the endoscope via the third or gas supply tube 560). Thus arranged, the fourth tube may be referred to as an alternative gas supply tube (e.g., $CO_2$).

With continued reference to FIGS. 5-7 and as will be described in greater detail below, in one embodiment, each of the plurality of tubes 530 may be sealed, capped, or the like to maintain a sterile environment prior to use. For example, each of the plurality of tubes 530 may include a seal 580 formed in or along the second end thereof to prevent fluid, moisture, air, etc. from entering into the container 520. Additionally, one or more tubes of other embodiments, such as those described with respect to FIGS. 11A-11C and/or 14A-14B, may incorporate one or more of the aspects and/or components to maintain a sterile environment without departing from this disclosure.

In addition, and/or alternatively, each of the plurality of tubes 530 may include, for example, a one-way valve 585 in the second end thereof. In use, the one-way valves 585 prevents backflow of fluid into the container 520. That is, incorporation of a one-way valve 585 into each of the second ends 544, 554, 564, 574 of the first, second, third, and fourth tubes 540, 550, 560, 570 ensures that the tubes are sealed to the surrounding environment ensuring that the container 520 remains sterile until operation. In one embodiment, the one-way valve 585 may be in the form of, for example, a Tuohy Borst adapter. In one embodiment, as will be described in greater detail below, in use, the one-way valves 585 may be arranged and configured to puncture or pierce the seal 580 formed in the tubes 530 when the one-way valves 585 are coupled thereto. For example, the one-way valves 585 may include a piercing or puncturing member for piercing the seal 580. Thus arranged, in use, coupling of the one-way valves 585 to the second ends 544, 554, 564, 574 of the first, second, third, and fourth tubes 540, 550, 560, 570 pierces the seal 580 formed in the tubes.

In addition, and/or alternatively, as illustrated, the second end of one or more of the plurality of tubes 530 may include, for example, an adapter, a connector, or the like 588 or the like, coupled to the second end thereof, either directly or indirectly via, for example, the one-way valve 585. That is, in one embodiment, the adapter 588 may be coupled directly to one or more of the second ends of the tubes. Alternatively, in one embodiment, the adapter 588 may be coupled to one or more of the one-way valves 585, which may be coupled to one or more of the second ends of the tubes. In one embodiment, in use, the adapter 588 may be arranged and configured to puncture or pierce the seal 580 formed in the tubes 530 when coupled directly thereto. For example, the adapter 588 may include a piercing or puncturing member for piercing the seal 580. Thus arranged, in use, coupling of the adapter 588 to the second ends of the tubes may pierce the seal 580 formed in the tubes.

In one embodiment, the adapter 588 may be in the form of, for example, an adjustable connector. For example, in one embodiment, as illustrated, the adapter 588 may be in the form of a stop-cock adaptor. In use, the stop-cock adaptor may be coupled, directly or indirectly, to the second end of one or more of the tubes 530. For example, as illustrated, in use, the alternative gas supply tube 570 may include a stop-cock adaptor. In use, a stop-cock adaptor may be manipulated by a user from a closed position to an opened position. Thus arranged, the user can enable gas and/or fluid flow through the respective tube by manipulating the stop-cock adaptor between the closed and opened positions. For example, in connection with the illustrated embodiment, the user may move the stop-cock adaptor from the closed position to the opened position to enable gas (e.g., $CO_2$) to flow from the $CO_2$ source into the container 520 via the alternative gas supply tube 570 to pressurize the container 520.

Alternatively, in one embodiment, the adapter 588 may be in the form of a coaxial split connector 590 coupled to the tube, either directly or indirectly. For example, in connection with the illustrated embodiment, a coaxial split connector 590 may be coupled, directly or indirectly, to the second end of the multi-lumen tube (e.g., the lens wash supply tube 550 and the gas supply tube 560) so that the second and third lumens 556, 566 may be coupled to the endoscope via the coaxial split connector 590. Thus arranged, in use, the coaxial split connector 590 is arranged and configured to couple to the endoscope so that fluid and gas may be exchanged with the endoscope. For example, in one embodiment, the coaxial split connector 590 may be arranged and configured to supply fluid and/or gas from the container 520 to the endoscope via the second and third lumens 556, 566, although this but one configuration. In one embodiment, the coaxial split connector 590 may be arranged and configured as, for example, a T-connector. The coaxial split connector 590 may be arranged and configured as an elastic or plastic end connector, to enable the second end of the tube to be coupled to, for example, the endoscope, gas source, or the like as needed. Alternatively, in one embodiment, the coaxial split connector 590 may be overmolded onto the tube, etc.

Thereafter, in use, with the integrated container and tube set 500 coupled to the endoscope, gas ($CO_2$) source, air pump, etc., the surgeon can operate, open, etc. the one-way valves, etc. to allow fluid and/or gas to flow. Subsequently, when demanded by the endoscope (e.g., when the surgeon actuates one or more of the various valves on the endoscope as—previously described in connection with FIG. 14), fluid and/or gas can be supplied to the endoscope depending on the procedural being performed.

Referring to FIG. 8A, an alternate embodiment of an integrated container and tube set 600 is disclosed. In accordance with one or more aspects of the present invention, the integrated container and tube set 600 is substantially similar to the integrated container and tube set 500 disclosed above in connection with FIGS. 4-7 except as outlined herein. Thus for the sake of brevity, detailed description of similar elements is omitted herefrom.

In accordance with one or more aspects of the present invention, the integrated container and tube set 600 includes a container 620 and a plurality of tubes 630. However, in contrast to the container 520 described above in connection with FIG. 5-7, the container 620 may be arranged in a non-rigid configuration (e.g., the container 620 may be arranged and configured as a compressible container). For example, the container 620 may be in the form of a pouch, a bag, or other soft fluid container similar to a saline style pouch (such terms being used interchangeably without intent to limit or otherwise convey different meaning or intent). Thus arranged, the non-rigid container 620 may be referred to as a pouch herein. In accordance with this embodiment, the tubes 630 may be molded to the pouch 620 while the pouch 620 is being manufactured. Thus arranged, the pouch 620 and tubes 630 may be manufactured from a suitable uniform material including, for example, plastics, elastomers, or any other suitable material now known or hereafter developed. Alternatively, in one embodiment, the pouch 620 may be separately formed from the tubes 630. For example, in one embodiment, the tubes 630 may be formed and the pouch 620 may be subsequently molded around the tubes 630. Thus arranged, a combined assembly could be manufactured. In this embodiment, the pouch 620 and tubes 630 may be manufactured from a suitable uniform material. Alternatively, the pouch 620 and tubes 630 could be manufactured from different materials.

Alternatively, referring to FIG. 8B, in one embodiment, the tubes 630 may be separately manufactured from the pouch 620. That is, the tubes 630 may be reversibly coupled to the pouch 620 (e.g., tubes 630 are arranged and configured to be inserted into the pouch 620 and may, in one embodiment, be removable therefrom). For example, in one embodiment, each of the tubes 630 may include a first end 632 including a piercing or penetrating member 634 arranged and configured to pierce a membrane or surface of the pouch 620 as the tubes 630 are being inserted, pressed, etc. into the pouch 620 to enable fluid and/or gas flow, as previously described. That is, in use, the first end 632 of the tubes 630 may include a piercing or penetrating member 634 such as, for example, a sharp tip or the like. Thus arranged, in use, the operating staff may insert one or more tubes 630 into the pouch 620 for supplying fluid and/or gas to the endoscope as desired.

In addition, and/or alternatively, in one embodiment, the plurality of tubes 630 may be arranged and configured as a multi-lumen tube. For example, the first irrigation supply tube, the second lens wash supply tube, the third gas supply tube, and the optional fourth alternative gas supply tube may be arranged and configured as a single tube at least along the first end thereof (e.g., a wall of each of the tubes may be coupled or integrally formed with each other). Alternatively, the first irrigation supply tube, the second lens wash supply tube, the third gas supply tube, and the optional fourth alternative gas supply tube may be separately formed and coupled together, or may remain separate and distinct with respect to each other.

In accordance with one or more aspects of the present disclosure, the pouch 620 can be filled during molding operations or post-molding operations. Thereafter, similar to the integrated container and tube set 500 previously described, the pouch 600 including the container 620 and tubes 630 may be used in place of the water reservoir 270 (e.g., water bottle) described above in connection with FIGS. 1-4.

Referring to FIGS. 9-10B, an alternate embodiment of an integrated container and tube set 700 is disclosed. In accordance with one or more aspects of the present invention, the integrated container and tube set 700 is substantially similar to the integrated container and tube sets 500 disclosed above in connection with FIGS. 4-7 except as outlined herein. Thus for the sake of brevity, detailed description of similar elements is omitted herefrom.

In accordance with one or more aspects of the present disclosure, the integrated container and tube set 700 includes a container 720 and a plurality of tubes 730. As illustrated, each of the tubes 730 may include a first end 732 disposed within the container 720 and a second end 734 positioned external to the container 720. In accordance with one or more aspects of the present disclosure, the second end 734 of the tubes 730 such as, for example, the second ends of the first irrigation supply tube, the second lens wash supply tube, the third gas supply tube, and the optional fourth alternative gas supply tube may be capped, closed, sealed, or the like 780 (such terms being used interchangeably without intent to limit or otherwise convey different meaning or intent) during manufacturing to create a permanent sealed assembly. Thereafter, in use, the second end 734 of the tubes 730 may be punctured by, for example, a piercing or penetrating member. For example, in one embodiment, the piercing or penetrating member may be in the form of one or more of the one-way valves, connectors, coaxial split connectors, or the like coupled to the second end 734 of the tubes 730. For example, in one embodiment and as schematically illustrated in FIGS. 10A and 10B, the coaxial split connector 590 may be arranged and configured to pierce or penetrate the sealed portion when the coaxial split connector 590 is coupled to the second end 734 of the tube.

The capped or sealed portion 780 may be configured along any length of the tube 730. For example, in one embodiment and as generally illustrated, the capped or sealed portion 780 may be positioned adjacent to an end portion of the second end 734 of the tubes 730, or at some point inside of the tube 730. In use, the valves, connectors, adapters, or the like may be arranged and configured to couple to the tube 730 via any suitable mechanism or method now known or hereafter developed. For example, the valves, connectors, or adapters may be press-fitted onto the tubes 730. Alternatively, anchoring methods such as, luer fittings, threaded connections, or the like, may be utilized. In either event, once coupled to the tubes 730, the valves, connectors or adapters are arranged and configured to create a seal with the tube 730 to prevent leaks at the puncture point.

Figure 11A:
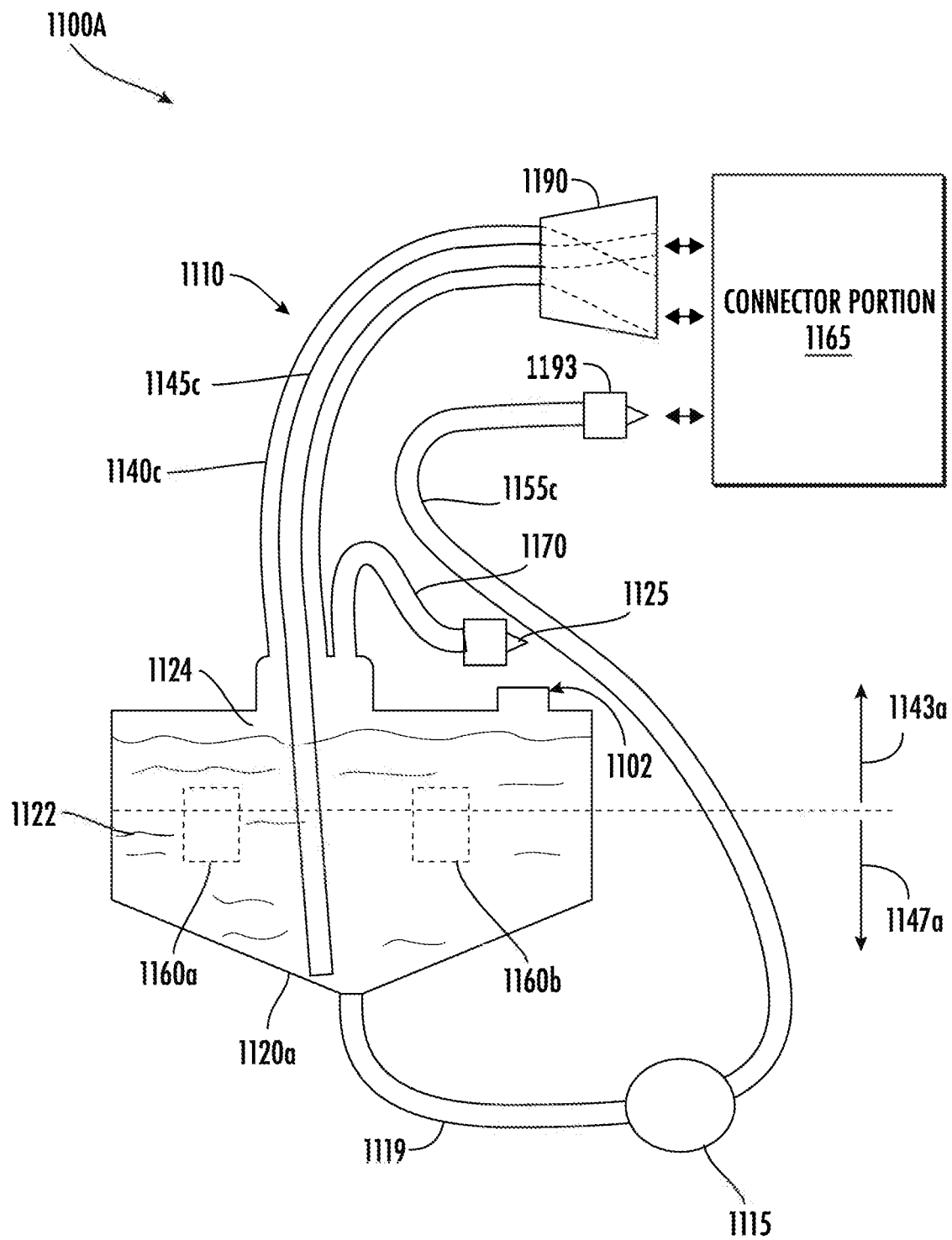
FIG. 11A depicts an integrated container and tube set or assembly suitable for use with an endoscope system, according to an embodiment of the present disclosure.
Figure 11B:
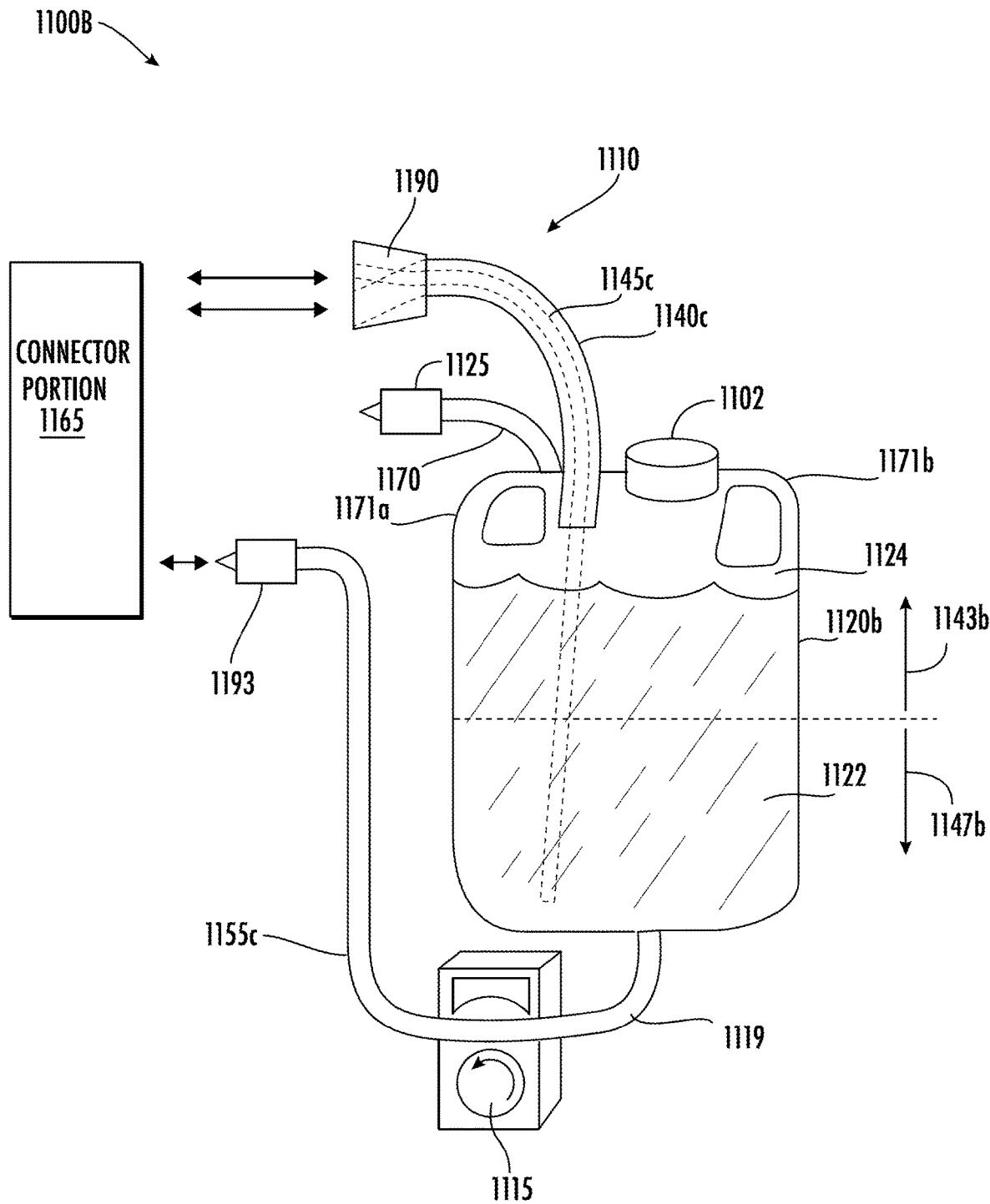
FIG. 11B depicts an integrated container and tube set or assembly suitable for use with an endoscope system, according to an embodiment of the present disclosure.
Figure 11C:
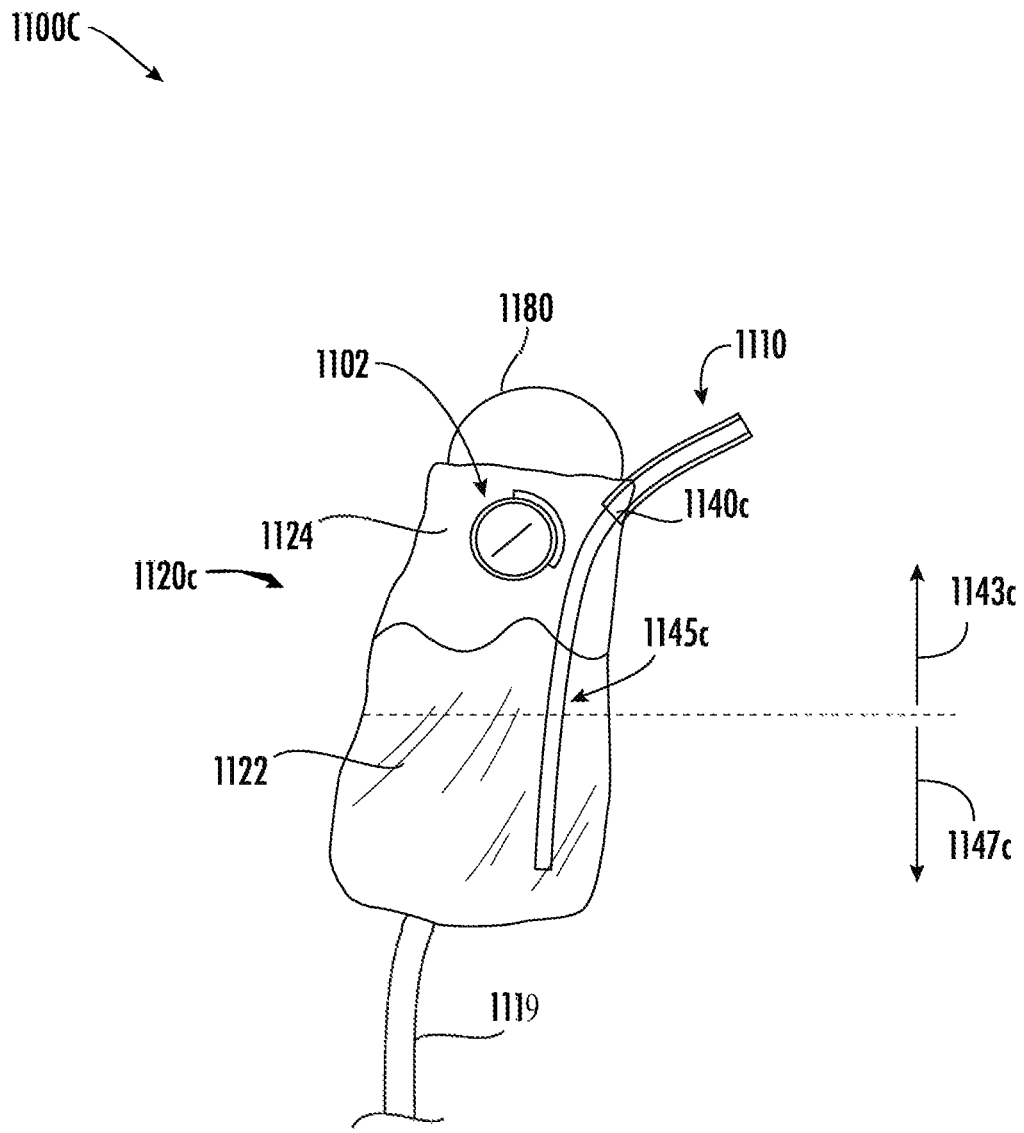
FIG. 11C depicts an integrated container and tube set or assembly suitable for use with an endoscope system, according to an embodiment of the present disclosure.

Referring to FIGS. 11A-11C, various embodiments of an integrated container and tube set 1100A, 1100B, 1100C are disclosed. In accordance with one or more aspects of the present invention, the integrated container and tube sets 1100A, 1100B, 1100C may be substantially similar to the integrated container and tube sets 500, 600, 700, 1400A, 1400B disclosed in connection with FIGS. 4-10A and 14A-14B except as outlined herein. Similarly, in accordance with one or more aspects of the present invention, one or more components, or features, of the integrated container and tube sets 1100A, 1100B, 1100C may be substantially similar to each other except as outlined herein. Thus for the sake of brevity, detailed description of similar elements may be omitted herefrom.

Generally, FIGS. 11A-11C illustrate an integrated container and tube set (i.e., 1100A, 1100B, or 1100C) that includes a gas/lens wash connection 1190, coaxial tubing 1110, a container (i.e., 1120a 1120b, or 1120c), upstream irrigation supply tubing 1119, an irrigation pump 1115, downstream irrigation supply tubing 1155c, an irrigation connection 1193, alternative gas supply tubing 1170, and an alternative gas connection 1125. Some embodiments may not include an alternative gas supply tubing 1170 or an alternative gas connection 1125 (see e.g., FIG. 11C). As shown in FIGS. 11A and 11B, gas/lens wash connection 1190 and irrigation connection 1193 may by removably couplable to connector portion 1165.

In many embodiments, connector portion 1165 may be the same or similar to connector portion 265, such as in FIGS.

2 and 4. In some embodiments, gas/lens wash connection 1190 may include a coaxial split connector having first and second opening. In some such embodiments, the first opening is in fluid communication with an inner tube of the coaxial tube (e.g., lens wash supply tubing 1145c) and the second opening is in fluid communication with an outer tube of the coaxial tube (e.g., gas supply tubing 1140c).

In FIG. 11A, the container 1120a may include an upper half 1143a, a lower half 1147a, and interfaces 1160a, 1160b. In FIG. 11B, the container 1120b may include upper half 1143b, lower half 1147b, and interface 1171a, 1171b. In FIG. 11C, the container 1120c may include upper half 1143c, lower half 1147c, and interface 1180. More generally, the upper halves of the containers may include a fill port 1102. In many embodiments, the fill port 1102 may be resealable. For example, fill port 1102 may include a removable cap or openable valve. In some embodiments, the fill port 1102 may include a check valve, such as in the removable cap. More generally, in various embodiments, a check valve may be included in the upper half of a container configured to equalize with atmospheric pressure. For example, when a rigid container is utilized a check valve may be included to prevent or limit a negative pressure differential with the atmosphere. The coaxial tubing 1110 and the alternative gas supply tubing 1170 may be coupled to the upper halves. In many embodiments, the outer tube of coaxial tubing 1110 (e.g., gas supply tubing 1140c) may couple to and terminate in the upper half of the container (e.g., 1143a of FIG. 11A) while the inner tube of coaxial tubing 1110 (e.g., lens wash tubing 1145c) may extend into and terminate in the lower half of the container (e.g., 1147a of FIG. 11A).

In various embodiments, one or more portions of the coaxial tubing 1110 and/or the alternative gas supply tubing 1170 may be integrally formed with the container. The upstream irrigation supply tubing 1119 may be coupled to the lower halves. In some embodiments, one or more portions of the irrigation supply tubing may be integrally formed with the container 1120a, 1120b, 1120c.

A liquid in a bottom portion 1122 of the containers may flow into either the upstream irrigation supply tubing 1119 or the lens wash tubing 1145c. In many embodiments, a gas may be introduced into a top portion 1124 of the containers, such as via gas supply tubing 1140c or alternative gas connection 1125, to force the liquid to flow into the lens wash tubing 1145c. In some embodiments, irrigation pump 1115 may be utilized to draw liquid from the container via upstream irrigation supply tubing 1119 and pump the liquid to the irrigation connection 1193 via downstream irrigation supply tubing 1155c. In many embodiments, irrigation pump 1115 many include a peristaltic pump. In some embodiments, the upstream irrigation supply tubing 1119 may be more rigid or robust than the downstream irrigation supply tubing. For example, upstream irrigation supply tubing may be more resistant to collapse than the downstream irrigation supply tubing.

Referring specifically to FIG. 11A, the container 1120a may be shaped such that upstream irrigation supply tubing couples to the container at a lowest point. The container 1120a may also include a downward wedge shape to facilitate the flow of fluid into the irrigation supply tubing. In some embodiments, container 1120a may include a width that is greater than its depth. For example, the width may be chosen to match the width of another component (e.g., irrigation pump, video processing unit, or cart) along with a narrow profile to provide an efficient and space saving configuration. In many embodiments, the container shape is chosen based on the component, or components, the interfaces are configured to couple to. The container 1120a may include one or more interfaces to couple with one or more of one or more of a mount, a hanger, and a holder. For example, interfaces 1160a, 1160b may include flat hooks that can couple to another component such as a pump, a video processing unit, or a cart.

Additionally, container 1120a may include a neck portion where the gas supply tubing 1140c and the alternative gas supply tubing 1170 couple to the container 1120a. In various embodiments, the neck portion may reduce, or prevent, flow of liquid 1122 from the container 1120a into the gas supply tubing 1140c and the alternative gas supply tubing 1170. In some embodiments, the container 1120a may be made from a rigid material. In another embodiment, the container 1120a may be made from a flexible material. In another such embodiment, the container 1120a may be collapsible. In many embodiments, the neck portion may be made from a more flexible material than the remainder of the container 1120a.

Referring specifically to FIG. 11B, the container 1120b may include one or more interfaces to couple with one or more of one or more of a mount, a hanger, and a holder. For example, interfaces 1171a, 1171b may include loops or handles that can be used for hanging the container 1120b, such as from an intravenous (IV) stand. In many embodiments, the interfaces 1171a, 1171b may be integrally formed with the container 1120b. In the illustrated embodiment, the interfaces 1171a, 1171b are disposed symmetrically with respect to a center line of the container 1120b.

Referring specifically to FIG. 11C, the container 1120c may include one or more interfaces to couple with one or more of a mount, a hanger, and a holder. For example, interface 1180 may include a loop or handle that can be used for hanging the container 1120c, such as from an IV stand. In many embodiments, the interface 1180 may be integrally formed with the container 1120c. In some embodiments, the fill port 1102 of container 1120c may be on a face. In some such embodiments, positioning the fill port 1102 on the front face may reduce the height required to refill the container 1120c and/or facilitate collapsibility of the container 1120c, such as by enabling it to fold flatter. In many embodiments, container 1120c is made from a flexible material. For example, container 1120c may be similar to an IV bag.

Figure 12:
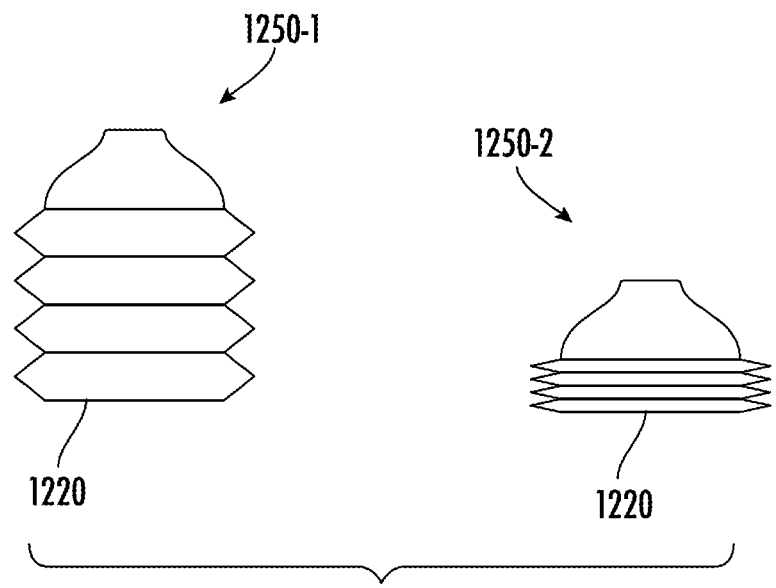
FIG. 12 depicts a container in first and second states, according to an embodiment of the present disclosure.

FIG. 12 depicts a container 1220 in a first state 1250-1 and in a second state 1250-2, according to an embodiment of the present disclosure. The container 1220 may be collapsible. Accordingly, state 1250-1 may represent an expanded state and state 1250-2 may represent a collapsed state. As previously mentioned, collapsibility may reduce storage space requirements. Further, collapsibility may reduce storage space requirements without sacrificing fluid holding capacity. More generally, the containers described hereby may include a capacity above 1 liter. For example, a container may have a capacity between 3 and 5 liters. In another example, a container may have a capacity of up to 8 liters. As previously mentioned, one or more containers described hereby may be flexible and/or collapsible. In some embodiments, the curved design of the necking portion may reduce, or prevent, flow of liquid from the container into gas supply tubes connected thereto.

Figure 13:
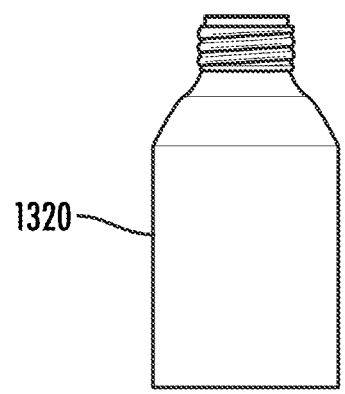
FIG. 13 depicts a container with a neck portion, according to an embodiment of the present disclosure.

FIG. 13 depicts a container 1320 with a neck portion, according to an embodiment of the present disclosure. In various embodiments, the staged design of the neck portion may reduce, or prevent, flow of liquid into the gas supply tubes connectable thereto. For example, the gradual, or stepped, reduction in diameter of the neck portion in the upper half of the container 1320. In some embodiments, an interface may be integrated into the neck portion. In one embodiment, the interface may include threads in the neck portion. For example, the threads may be utilized to couple with an interface of an endoscopic system.

Figure 14A:
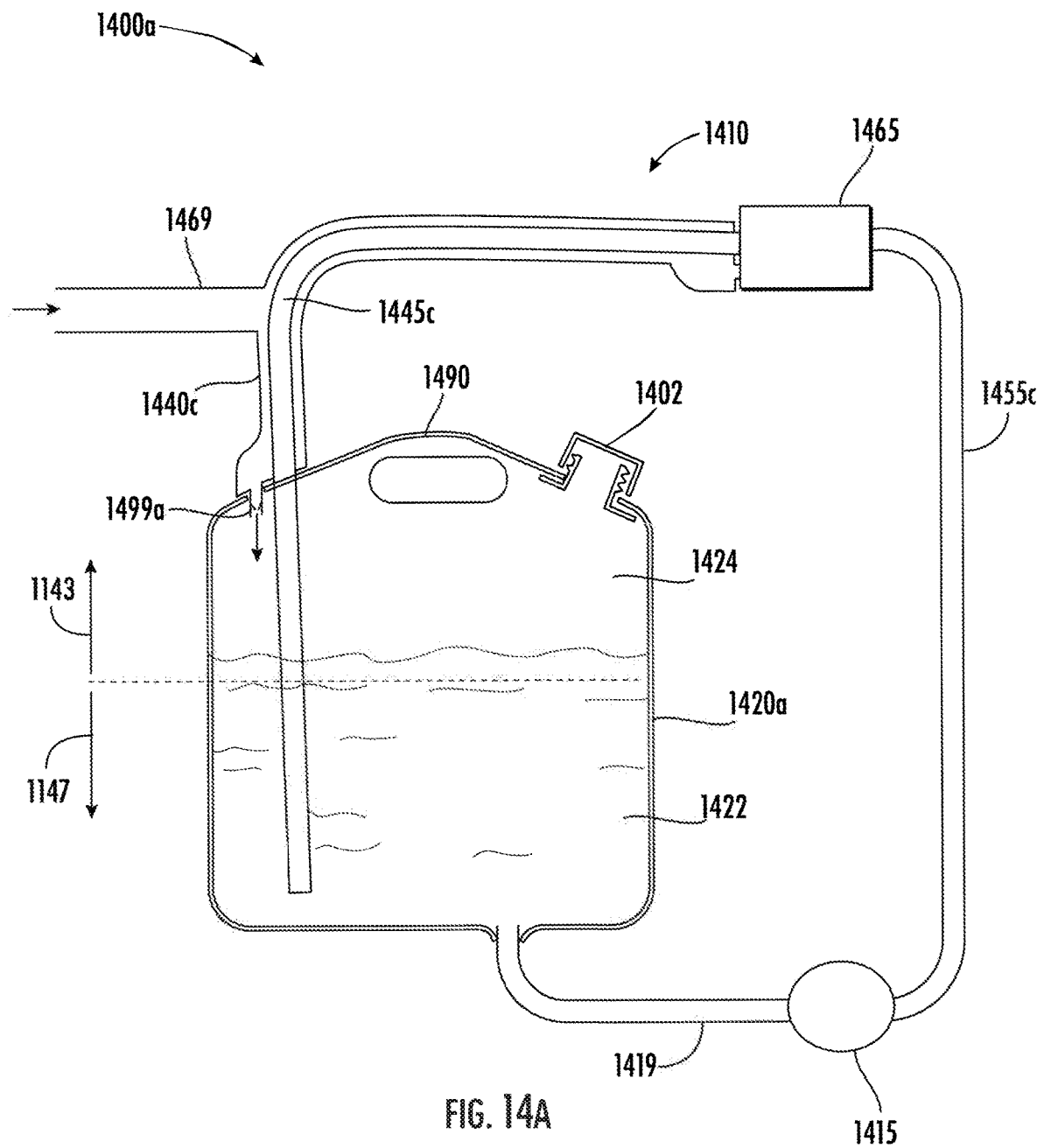
FIG. 14A depicts an integrated container and tube set or assembly comprising a check valve suitable for use with an endoscope system, according to an embodiment of the present disclosure.
Figure 14B:
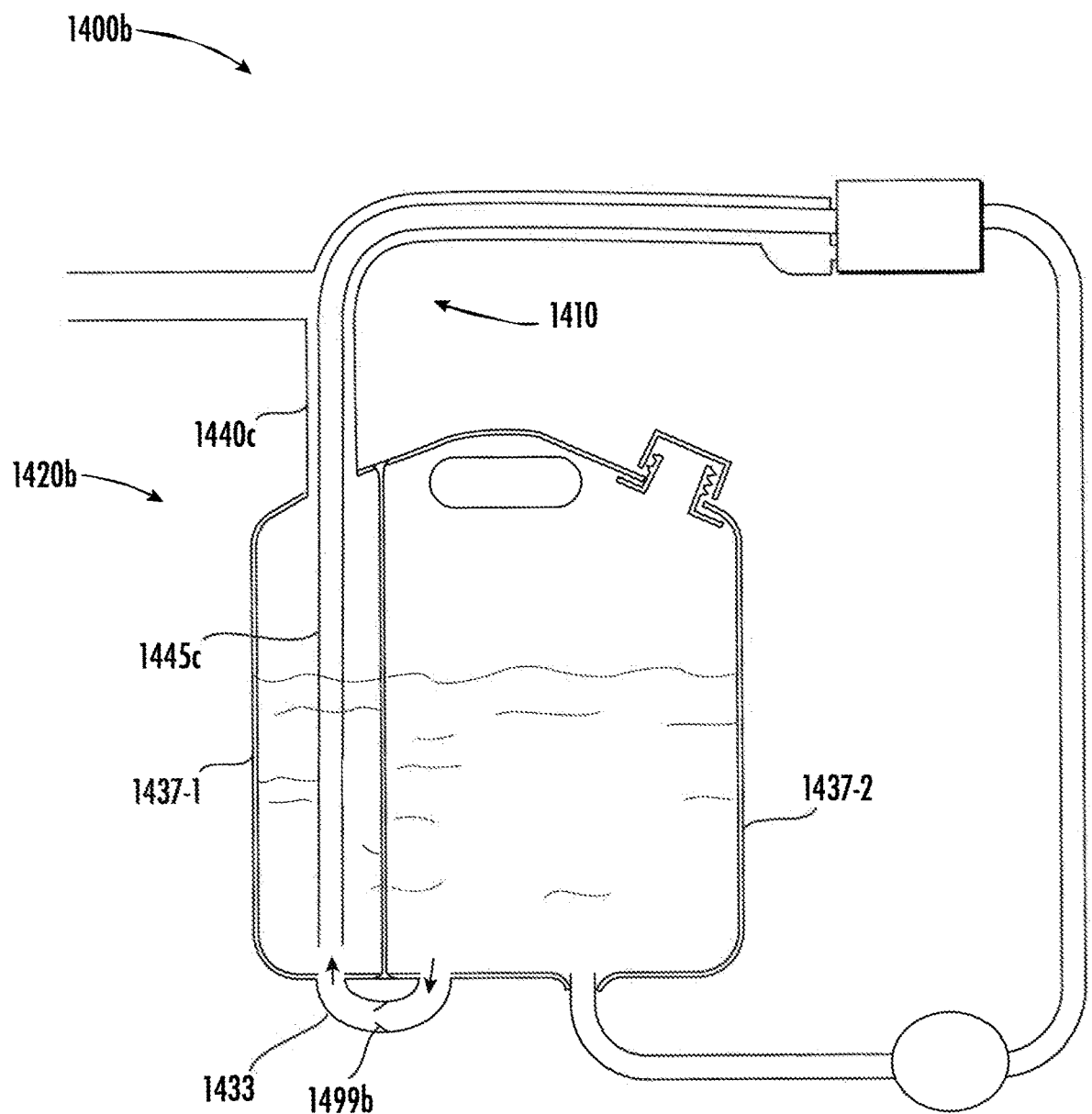
FIG. 14B depicts an integrated container and tube set or assembly comprising a two-chamber container suitable for use with an endoscope system, according to an embodiment of the present disclosure.

Referring to FIGS. 14A and 14B, embodiments of an integrated container and tube sets 1400A, 1400B are disclosed. In accordance with one or more aspects of the present invention, the integrated container and tube sets 1400A, 1400B may be substantially similar to the integrated container and tube sets 500, 600, 700, 1100A, 1100B, 1100C disclosed above in connection with FIGS. 4-11C, except as outlined herein. Similarly, in accordance with one or more aspects of the present invention, one or more components, or features, of the integrated container and tube sets 1400A, 1400B may be substantially similar to each other except as outlined herein. Thus, for the sake of brevity, detailed description of similar elements may be omitted herefrom.

Generally, FIGS. 14A and 14B illustrate an integrated container and tube set (i.e., 1400A or 1400B) that includes connector portion 1465, coaxial tubing 1410 with gas supply tubing 1440c and lens wash tubing 1445c, gas source supply tubing 1469, container 1420a, 1420b with upper half 1443 and lower half 1447, upstream irrigation supply tubing 1419, irrigation pump 1415, and downstream irrigation supply tubing 1455c. Additionally, the container 1420a, 1420b may include fill port 1402 and interface 1490. In many embodiments, connector portion 1465 may be the same or similar to connector portion 265, such as in FIGS. 2 and 4. The integrated container and tube set 1400A includes features to maintain a gas pressure within at least a portion of the container 1420a. The integrated container and tube set 1400B includes features to facilitate quick pressure buildup within at least a portion of the container 1420b. In many embodiments, these features may be used separately, or in combination, to reduce lag in lens wash functionality provided via lens wash tubing 1445c. For example, maintaining a gas pressure within at least a portion of the container reduces the amount of gas that must be introduced into the portion of the container (e.g., into top portion 1424) in order to make a liquid (e.g., in bottom portion 1422) flow up the lens wash tubing 1445c, out of the container, and out of a lens wash outlet (e.g., gas/lens wash outlet 220 of FIG. 2). Accordingly, various embodiments may have a response time for the lens wash functionality of five seconds or less, such as one second. In various embodiments, the response time may refer to an amount of time from activating the lens wash functionality (e.g., by depressing gas/water valve 140 of FIG. 2) until liquid begins to flow out of the endoscopic system (e.g., via gas/lens wash outlet 220 of FIG. 2).

In FIG. 14A, a check valve 1499a is included wherein the gas supply tubing 1440c couples to the container 1420a. In various embodiments, the check valve 1499a may prevent gas from escaping the top portion 1424 of the container 1420a. In other words, the check valve 1499a may only allow flow from the gas supply tubing 1440c (e.g., air from connector 1465 or $CO_2$ from gas source supply tubing 1469) into the interior of the container 1420a. In many embodiments, a pressure inside the top portion 1424 may remain closer to a pressure necessary to force liquid in the bottom portion 1422 up the lens wash tubing 1445c and out of the container 1420a due to the check valve 1499a. Accordingly, lens wash functionality may be more responsive than if the pressure in the container had to be built up from a lower pressure (e.g., as a result of pressure bleeding to atmosphere when a physician is calling for neither air, nor lens watch with the air/water valve on the endoscope). For example, check valve 1499a may enable the container 1420a to remain at a pressure between 1 and 8 psi (above atmospheric pressure), instead of falling back to atmospheric pressure.

Additionally, in integrated container and tube set 1400A, a gas, may be provided via the gas source supply tubing 1469 instead of via connector portion 1465 or via an alternative gas supply tube as described above. In some such embodiments, the gas source supply tubing 1469 may effectively be the same as an alternative gas supply tube, the only difference being that gas may not be provided via a connector portion, such as from pressurizing pump 215 of endoscopic system 200. More generally, various embodiments described hereby may function in this manner without departing from the scope of this disclosure. In some such embodiments, a pressurizing pump separate from connector 1465 may be attached to the gas source supply tubing 1469. In other such embodiments, a pressurized canister (e.g., of air, oxygen, $CO_2$, etcetera) may be attached to the gas source supply tubing. Similarly, integrated container and tube sets 1400A, 1400B may utilize a connector portion 1465 and/or an alternative gas supply tube without departing from the scope of this disclosure.

In some embodiments, a coaxial split connector may be utilized to couple coaxial tubing 1410 with container 1420a. The coaxial split connector may enable a standard check valve to be utilized. Alternatively, an umbrella style check valve could be used while the gas supply tubing 1440c and lens wash tubing 1445c remained coaxial.

In FIG. 14B, the container 1420b includes a first chamber 1437-1 and a second chamber 1437-2. The first chamber 1437-1 may be connected to the second chamber 1437-2 via a side channel 1433. The side channel 1433 may include a check valve that only allows flow from the second chamber 1437-2 to the first chamber 1437-1. Container 1420b may include the first chamber 1437-1 to provide a small volume in which to build pressure by introducing gas via gas supply tubing 1440c, but at the same time container 1420b facilitates a larger overall volume of available liquid in chamber 1437-2.

In many embodiments, with the much smaller first chamber 1437-1, there is less volume of air in which to build pressure to deliver lens wash, even if the water level has already been drawn down to low level, e.g., less than quarter of the second chamber 1437-2. In this way undesirably long response time between calling for lens wash and delivering to scope is prevented.

In several embodiments, once the pressure in chamber 1437-1 falls low enough, the head pressure created by having a higher level of fluid in chamber 1437-2 may create a flow from the second chamber 1437-2 into the first chamber 1437-1 to refill the first chamber 1437-1 back to a level equal to the second chamber 1437-2. Additionally, or alternatively, when the container is sufficiently flexible, the second chamber 1437-2 may be squeezed manually to force water from the second chamber 1437-2 into the first chamber 1437-1. Accordingly, the container 1420b may be flexible and/or collapsible. In some embodiments a second check valve may be included such as described with respect to FIG. 14A. In some such embodiments, an umbrella style check valve may be utilized in coaxial tubing 1410. A fill port 1402 in second chamber 1437-2 allows for that chamber to be refilled. In many embodiments, fill port 1402 is the same or similar to fill port 1102. If the container 1420b is sufficiently flexible, pressure can be drawn down in the second chamber 1437-2 by operation of the irrigation pump 1415, collapsing the second chamber 1437-2, without affecting pressure in the first chamber 1437-1. If the container 1420b is more rigid, and collapsing of the container is not desired, then a one-way vent can be included in the second chamber (e.g., as part of the fill port 1402) to allow atmospheric air to be pulled into the chamber when the irrigation pump is operating, thus keeping the pressure at a level that the second chamber doesn't collapse. In either case, the pressure in the first chamber is unaffected because check valve 1199b presents liquid from being pulled from the first chamber into the second chamber.

In the illustrated embodiment, the side channel 1433 includes a u-shaped connection between the first chamber 1437-1 and second chamber 1437-2. However, the side channel 1433 may be configured in a variety of ways without departing from the scope of this disclosure. For example, the side channel 1433 may be positioned against, or within, the bottom wall of the container 1420b. In another example, the side channel 1433 may include an opening in the wall dividing the first and second chambers 1437. In such examples, check valve 1499b may be disposed in the opening in the wall. In many embodiments, the side channel 1433 may be integrally formed with the container 1420b. In one embodiment, a side channel may not be included. For example, each chamber may have a separate fill port. In some embodiment, the side channel 1433 may be included along with separate fill ports for both chambers to provide different avenues for refilling first chamber 1437-1. In one embodiment, the first chamber 1437-1 may have a capacity between 0.5 and 2 liters, such as 1 liter, and the second chamber 1437-2 may have a capacity between 1.5 and 8 liters, such as 4 liters.

Exemplary devices, systems, and methods with which embodiments of the present disclosure may be implemented include, but are not limited to, those described in U.S. Patent Application, titled "Tubing Assemblies and Methods for Fluid Delivery", filed even date herewith, the complete disclosure of which is incorporated by reference herein in its entirety.

As will be appreciated, the lengths of irrigation, lens wash, gas supply, alternate gas supply tubing may have any suitable size (e.g., diameter). In addition, the sizing (e.g., diameters) of the tubing may vary depending on the application. In one non-limiting embodiment, the irrigation supply tubing may have an inner diameter of approximately 6.5 mm and an outer diameter of 9.7 mm. The lens wash supply tubing may have an inner diameter of approximately 5 mm and an outer diameter of 8 mm. The gas supply tubing may have an inner diameter of approximately 2 mm and an outer diameter of 3.5 mm. The alternative gas supply tubing may have an inner diameter of approximately 5 mm and an outer diameter of 8 mm.

It will be apparent to those skilled in the art that various modifications and variations can be made to the disclosed device without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

All apparatuses and methods discussed herein are examples of apparatuses and/or methods implemented in accordance with one or more principles of this disclosure. These examples are not the only way to implement these principles but are merely examples. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure.

In the foregoing description and the following claims, the following will be appreciated. The phrases "at least one", "one or more", and "and/or", as used herein, are open-ended expressions that are both conjunctive and disjunctive in operation. The term "a" or "an" entity, as used herein, refers to one or more of that entity. As such, the terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader's understanding of the present disclosure, and/or serve to distinguish regions of the associated elements from one another, and do not limit the associated element, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another.

The foregoing discussion has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. One skilled in the art will appreciate that the disclosure may be used with many modifications of structure, arrangement, proportions, materials, components, and otherwise, used in the practice of the disclosure, which are particularly adapted to specific environments and operative requirements without departing from the principles of the present disclosure. For example, elements shown as integrally formed may be constructed of multiple parts or elements shown as multiple parts may be integrally formed, the operation of elements may be reversed or otherwise varied, the size or dimensions of the elements may be varied, and features and components of various embodiments may be selectively combined. The presently disclosed embodiments are therefore to be considered in all respects as illustrative and not restrictive, the scope of the claimed invention being indicated by the appended claims, and not limited to the foregoing description.

The following claims are hereby incorporated into this Detailed Description by this reference, with each claim standing on its own as a separate embodiment of the present disclosure. In the claims, the term "comprises/comprising"

does not exclude the presence of other elements or steps. Furthermore, although individually listed, a plurality of means, elements or method steps may be implemented by, e.g., a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second", etc., do not preclude a plurality. Reference signs in the claims are provided merely as a clarifying example and shall not be construed as limiting the scope of the claims in any way.

What is claimed is:

1. An integrated container and tube set arranged and configured to couple to an endoscope for use in an endoscopic procedure, the integrated container and tube set comprising:
    a container configured to contain a fluid, the container having side walls, a bottom portion, and a top portion;
    a lens wash supply tube including a first end, a second end, and a first lumen extending therethrough, wherein the first lumen is in fluid communication with the bottom portion of the container and the second end of the lens wash supply tube is positioned external to the container; and
    a gas supply tube having a wall that is integrally molded to a side wall of the container, the gas supply tube including a first end, a second end, and a second lumen extending therethrough, wherein the second lumen is in operative communication with the top portion and the second end of the gas supply tube is positioned external to the container.

2. The integrated container and tube set of claim 1, wherein the lens wash supply tube and the gas supply tube are arranged and configured as a multi-lumen tube.

3. The integrated container and tube set of claim 2, wherein the first lumen is coaxial with the second lumen, with the first lumen positioned within the second lumen.

4. The integrated container and tube set of claim 2, wherein the multi-lumen tube further comprises an internal wall extending along a length thereof between the first lumen and the second lumen so that the second lumen extends adjacent to the first lumen.

5. The integrated container and tube set of claim 1, further comprising an irrigation supply tube having a first end, a second end, and a third lumen extending therethrough, wherein the first end of the irrigation supply tube is permanently coupled to the container, the first end of the irrigation supply tube being arranged and configured to be in fluid communication with the bottom portion of the container, and the second end of the irrigation supply tube is positioned external to the container.

6. The integrated container and tube set of claim 1, wherein one or more of the second ends of the lens wash supply tube and the gas supply tube are sealed.

7. The integrated container and tube set of claim 1, wherein one or more of the second ends of the lens wash supply tube and the gas supply tube are arranged and configured with a one-way valve.

8. The integrated container and tube set of claim 7, wherein at least one of the lens wash supply tube and the gas supply tube includes an adjustable connector coupled thereto, the adjustable connector moveable between a closed position and an opened position.

9. The integrated container and tube set of claim 8, further comprising an endoscope adapter coupled to the lens wash supply tube and the gas supply tube, the endoscope adapter comprising a lumen in fluid communication with the first lumen and a gas lumen in communication with the second lumen, the endoscope adapter configured to interface with an endoscope.

10. The integrated container and tube set of claim 1, further comprising a supply port formed in the container.

11. An integrated container and tube set arranged and configured to couple to an endoscope for use during an endoscopic procedure, the integrated container and tube set comprising:
    a container configured to contain a fluid, the container having side walls, a bottom portion, and a top portion;
    a lens wash supply tube including a first end, a second end, and a first lumen extending through the first end of the lens wash supply tube and along a length of the lens wash supply tube toward the second end of the lens wash supply tube, wherein the first end of the lens wash supply tube is in fluid communication with the bottom portion of the container and the second end of the lens wash supply tube is closed to the first lumen; and
    a gas supply tube having a wall that is integrally molded to a side wall of the container, the gas supply tube including a first end, a second end, and a second lumen extending through the first end of the gas supply tube and along a length of the gas supply tube toward the second end of the gas supply tube, wherein the first end of the gas supply tube is in operative communication with the top portion of the container and the second end of the gas supply tube is closed to the second lumen.

12. The integrated container and tube set of claim 11, wherein each second end of each of the lens wash supply tube and the gas supply tube are configured to be penetrated by an adapter member.

13. The integrated container and tube set of claim 11, wherein one or more of the second ends of the lens wash supply tube and the gas supply tube are arranged and configured with a one-way valve.

14. The integrated container and tube set of claim 11, further comprising an irrigation supply tube having a wall that is integrally molded to a side wall of the container, the irrigation supply tube including a first end, a second end, and a third lumen extending through the first end and along a length of the irrigation supply tube toward the second end of the irrigation supply tube, wherein the first end of the irrigation supply tube is in fluid communication with the bottom portion of the container and the second end of the irrigation supply tube is closed to the third lumen.

15. An integrated container and tube set arranged and configured to couple to an endoscope for use in an endoscopic procedure, the container and tube set comprising:
    a container configured to contain a fluid, the container having an upper half and a lower half, wherein the upper half includes a fill port;
    a coaxial tube coupled to the upper half of the container, the coaxial tube comprising an inner tube and an outer tube, wherein the inner tube comprises a lens wash supply tube and terminates in the upper half of the container, wherein the outer tube comprises a gas supply tube and terminates in the lower half of the container, and
    wherein the outer tube is integrally formed with the container.

16. The integrated container and tube set of claim 15, further comprising an irrigation supply tube coupled to the lower half of the container, wherein the irrigation supply tube terminates in the lower half of the container.

17. The integrated container and tube set of claim 15, wherein the container includes an interface configured to couple the container to one or more of a mount, a hanger, and a holder.

18. The integrated container and tube set of claim 17, wherein the interface comprises a hook or a loop in the upper half of the container.

19. The integrated container and tube set of claim 15, further comprising a gas/lens wash connection attached to an end of the coaxial tube and configured to interface with the endoscope.

20. The integrated container and tube set of claim 19, wherein the gas/lens wash connection includes a coaxial split connector comprising a first opening and a second opening, the first opening in fluid communication with the inner tube and the second opening in fluid communication with the outer tube.

* * * * *